United States Patent [19]

Michaels et al.

[11] Patent Number: 4,992,409
[45] Date of Patent: Feb. 12, 1991

[54] CATALYST AND METHOD OF PREPARING THE CATALYST FOR LOWER ALKANE CONVERSION

[75] Inventors: Glenn O. Michaels, South Holland; Michael J. Spangler, Sandwich, both of Ill.

[73] Assignee: Amoco Corporation, Chicago, Ill.

[21] Appl. No.: 295,502

[22] Filed: Jan. 11, 1989

[51] Int. Cl.$^5$ .................. B01J 21/04; B01J 23/02; B01J 23/04
[52] U.S. Cl. .................. 502/341; 502/243; 502/340; 502/343
[58] Field of Search .............. 502/243, 340, 341, 343

[56] References Cited

U.S. PATENT DOCUMENTS

| | | | |
|---|---|---|---|
| 4,450,310 | 5/1984 | Fox et al. | 502/340 X |
| 4,672,145 | 6/1987 | Kolts et al. | 502/340 X |
| 4,774,216 | 9/1988 | Kolts et al. | 502/340 X |
| 4,780,449 | 10/1988 | Hicks | 502/341 X |
| 4,795,842 | 1/1989 | Gaffney et al. | 585/400 |

*Primary Examiner*—W. J. Shine
*Attorney, Agent, or Firm*—Nick C. Kottis; William H. Magidson; Ralph C. Medhurst

[57] ABSTRACT

A method for converting a feedstock alkane containing from 1 to 3 carbon atoms to a higher molecular weight hydrocarbon comprising contacting a feedstock with an oxygen-containing gas in the presence of a catalytic composition is disclosed. The catalytic composition includes a Group IA metal, a Group IIA metal and a third component, the precursor of which is a sol such as an aqueous suspension of a metal such as aluminum, silicon, titanium, zinc, zirconium, cadmium or tin with which the other components of the composition are thoroughly dispersed.

25 Claims, 1 Drawing Sheet

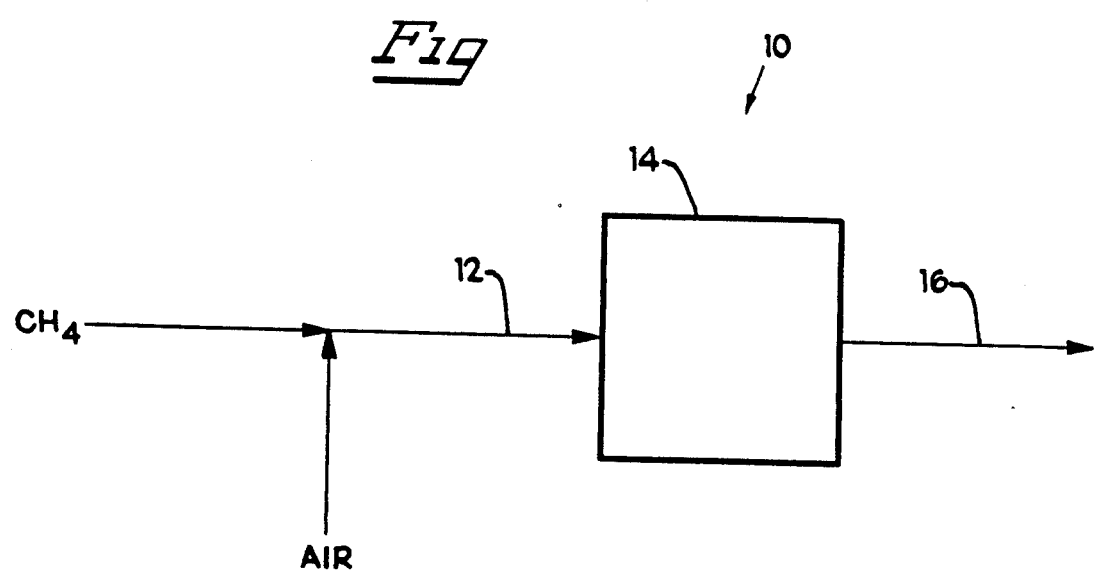

CATALYST AND METHOD OF PREPARING THE CATALYST FOR LOWER ALKANE CONVERSION

BACKGROUND OF THE INVENTION

This invention relates generally to the utilization of lower alkanes and the synthesis of hydrocarbons therefrom and, more specifically, to conversion of a low molecular weight alkane, such as methane, to a higher molecular weight hydrocarbon.

As the uncertain nature of ready supplies and access to crude oil has become increasingly apparent, alternative sources of hydrocarbons and fuel have been sought out and explored. The conversion of low molecular weight alkanes (lower alkanes) to higher molecular weight hydrocarbons has received increasing consideration as such low molecular weight alkanes are generally available from readily secured and reliable resources. Natural gas, partially as a result of its comparative abundance, has received a large measure of the attention focused on sources of low molecular weight alkanes. In addition, low molecular weight alkanes are generally present in coal deposits and may be formed during numerous mining operations, in various petroleum processes, and in the above- or below-ground gasification or liquefaction of coal, tar sands, oil shale and biomass, for example. Generally, however, much of the readily accessible natural gas has a high valued use as a fuel whether in residential, commercial or industrial applications.

Additional major natural gas resources, however, are prevalent in many remote portions of the world such as remote areas of Western Canada, Australia, U.S.S.R. and Asia. Commonly, natural gas from these types of resources is referred to as "remote gas." Of course accessibility is a major obstacle to effective and extensive use of remote gas. Consequently, methods for converting low molecular weight alkanes, such as those present in remote gas, to higher molecular weight hydrocarbons, preferably, to more easily transportable liquid fuels, are desired and a number of such methods have been reported.

For example, G. E. Keller and M. M. Bhasin (J. Catal., 73, 1982, 9–19) have shown that methane can be converted to $C_2$ hydrocarbons in the presence of reducible metal oxide catalysts but that the yields of ethylene and ethane are low and amount to only from 10 to 50 percent of the reacted methane. To improve the selectivity for the production of the desired $C_2$ hydrocarbons and to suppress the undesirable further reaction of the $C_2$ hydrocarbons initially formed to carbon dioxide, Keller and Bhasin proposed a special reaction method generally involving a sequence of four steps;

(1) charging the catalyst with oxygen by passing an oxygen-containing gas over the catalyst;

(2) replacing the oxygen in the gas chamber of the catalytic reactor with an inert gas;

(3) feeding methane over the catalyst, which partially produces the desired reaction; and (4) supplanting the residual methane and resulting product in the reactor with an inert gas before the sequence of steps is repeated.

In this process, depending on the catalyst used and the temperature selected, the selectivities for the production of $C_2$ hydrocarbons range from about 5% to about 45%, the selectivities for the production of $CO_2$ range from about 55% to 95%, and the conversions of methane range between 1% and 10%.

Keller and Bhasin arrived at the conclusion that oxidative coupling is only highly selective to higher hydrocarbons when the coupling reaction takes place in the absence of gas-phase oxygen and that the oxidative coupling of the hydrocarbons should be caused by reaction with the lattice oxygen of the metal oxide "catalyst," resulting in the reduction of the valence level of the metal oxide. [NOTE: The term "catalyst" as used herein does not have its standard meaning as while a relatively small amount of the specified material notably affects the rate of the chemical reaction, the material itself or at least a component thereof is consumed or undergoes a chemical reaction.] Thus, since the catalyst has only a predetermined amount of lattice oxygen available, only a limited quantity of hydrocarbon can be reacted for every measured unit of catalyst before the catalyst needs to be regenerated, e.g., with oxygen being taken up by lattice openings.

It is evident that the modus operandi in Keller and Bhasin is costly in terms of apparatus as well as simultaneously being linked with relatively smaller yields in space-time terms and high operating and investment costs. Moreover, according to the data of the authors, the attainable methane conversions and/or the resultant spacetime yields are generally believed to be too small for commercial installations. Furthermore, the only products reported are $C_2$ hydrocarbons.

Subsequent to the publication of the findings of Keller and Bhasin, the efforts of a number of other researchers in the area of oxidative coupling have been reported, published and/or patented. For example, Jones et al., U.S. Pat. Nos. 4,443,664-9 disclose methods for synthesizing hydrocarbons containing as many as 7 carbon atoms from a methane source which comprise contacting methane with a reducible oxide of antimony, germanium, bismuth, lead, indium or manganese. These patents also disclose that the reducible oxides can be supported by a conventional support material such as silica, alumina, titania and zirconia. The ranges of reaction temperatures disclosed in the aforesaid patents are from a lower limit 500° C. to an upper limit of 800° C.–1000° C. In the disclosed processes (hereinafter referred to as a "redox" process or mode of operation), the reducible oxide is first reduced and then regenerated by oxidizing the reduced composition with molecular oxygen, either in a second zone or by alternating the flow of the feed gas, e.g., a methane-containing gas, with the flow of an oxygen-containing gas. The highest yield of hydrocarbon products reported was only about 2.1% of the methane feed, when a reducible oxide of manganese was employed.

Baerns, West German Patent Application No. 3,237,079.2, discloses a method for the production of ethane or ethylene by the reaction of methane and oxygen-containing gas at a temperature between 500° C. and 900° C., at an oxygen partial pressure of less than about 0.5 atmosphere at the reactor entrance, with a ratio of methane partial pressure to oxygen partial pressure greater than 1 at the reactor entrance and in the presence of a solid catalyst free of acidic properties. As disclosed, the method can be performed with or without recycle of remaining unreacted methane. The highest molecular weight product formed in the disclosed method is propane and the highest collective selectivity for the formation of ethane, ethylene and propane is only about 65% of methane converted.

Baerns discloses that oxides of metals of Groups III and VII of the Periodic Table are suitable for use as catalysts in the methods disclosed therein and that the oxides of lead, manganese, antimony, tin, bismuth, thallium, cadmium and indium are particularly preferred. Baerns further discloses that the metal oxides can be employed with or without a carrier and that specifically preferred carriers are alumina, silica, silica carbide and titania. Specific examples of carrier materials disclosed were formed from gamma-alumina having BET surface areas of 160–166 m$^2$/gm, silica having a BET surface area of 290 m$^2$/gm, bismuth oxide, alumina silicate and titania.

Ito et al., "Synthesis Of Ethylene and Ethane By Partial Oxidation of Methane Over Lithium-Doped Magnesium Oxide," Nature, Vol. 314, (April 25, 1985) 721–722, discusses the use of lithium-doped magnesium oxide in the partial oxidation of methane to more useful chemicals such as higher molecular weight hydrocarbons including methanol, ethylene, and benzene. Therein, a yield of 19% for C$_2$ compounds with 50.3% selectivity at 37.8% conversion was reported and noted to be considerably better than the results reported in the literature for other metal oxides.

Ito et al., "Oxidative Dimerization Of Methane Over A Lithium-Promoted Magnesium Oxide Catalyst," J. Am. Chem. Soc., Vol. 107, (1985) 5062–5068, discusses the use of lithium-promoted magnesium oxide in the conversion of methane to higher molecular weight hydrocarbons such as ethane and ethylene, for example. Therein, C$_2$ compounds obtained with 50% selectivity at a 38% conversion of CH$_4$ over 4 grams of a catalyst having 7 wt. % lithium-promoted magnesium oxide at 720° C. were reported. It is noted that better selectivities for C$_2$ (ca. 70%) were achieved over catalysts promoted with 7% or more Li$^+$. The article advances a model for the selective conversion of CH$_4$ wherein the major part of the activity results from the substitution of a monovalent cation into a divalent site and thus calls for the alkali metal ion to be substitutable for the alkaline earth ion.

International Publication WO 86/05176 broadly discloses a method for converting a feedstock alkane containing from one to three carbon atoms to higher molecular weight hydrocarbons. The method includes the steps of contacting the feedstock alkane with an oxygen-containing gas in a reactor in a presence of an oxidative coupling catalyst to produce a gaseous mixture including higher molecular weight saturated and unsaturated aliphatic hydrocarbon products followed by contacting the resulting gaseous mixture with an oligomerization catalyst. Oxidative coupling catalysts disclosed to be useful in the practice in the invention include silica having a surface area of less than about 175 m$^2$/gm and reducible compounds of lead, antimony, germanium, vanadium, tin, bismuth, cadmium, indium, manganese, thallium or mixtures thereof.

The publication, 8th International Congress on Catalysis, in an article entitled, "Oxidative Dehydrogenation and Coupling of Methane," Hinsen et al., pp. 581–593 (July, 1984) describes a process for the oxidative coupling of methane utilizing a PbO supported catalyst. Various supports were tested, including: $\gamma$ and $\alpha$-Al$_2$O$_3$, TiO$_2$, alumina silicate and silica gel. These support materials had very high surface areas, ranging, for example, from 110 m$^2$/g for $\gamma$-Al$_2$O$_3$ up to 245 m$^2$/g for the SiO$_2$ gel with the catalyst typically being prepared by incipient wetness techniques whereby the pores in the support material are filled with liquid. The use of such high surface area materials in catalysts to be used for oxidative coupling is generally undesirable as the resulting high surface area catalysts typically have relatively high selectivity to "combustion products," such as CO and CO$_2$. In oxidative coupling, the formation of such combustion products is generally sought to be minimized as the formation of such carbon-containing combustion products is typically viewed as being at the expense of reduced production of desired higher molecular weight hydrocarbons.

Over the years various additional oxidative coupling catalyst, contact agent, contact solid or the like compositions; additives, promoters, or the like for addition thereto and processes for oxidative coupling have been tested, reported or disclosed with varying degrees of success. Typifying these materials are those found in U.S. Pat. Nos. 4,444,984; 4,533,780; 4,547,607; 4,554,395; 4,567,307; and 4,568,785.

More particularly, U.S. Pat. Nos. 4,489,215; 4,495,374; 4,499,322; 4,499,323; 4,499,324; 4,450,310; 4,523,049; 4,656,155; 4,721,828; and 4,727,212; while disclosing processes utilizing compositions which include an alkali metal, an alkaline earth metal or combinations thereof, require, as a key component, a reducible metal oxide and/or depend on the utilization of lattice oxygen.

For example, U.S. Pat. No. 4,450,310 discloses a methane conversion process for the production of olefins and hydrogen wherein methane is contacted with a catalyst including the mixed oxides of a Group IA metal, a Group IIA metal and optionally a promoter metal, such as copper, rhenium, tungsten, zirconium, rhodium and mixtures thereof, in the absence of oxygen and water, to produce olefins and hydrogen. Thus, the contacting of methane with the catalyst material is done in the absence of oxygen.

U.S. Pat. No. 4,523,049 discloses a method for converting methane to higher hydrocarbon products wherein a methane-containing hydrocarbon gas and an oxygen-containing gas are contacted with a reducible metal oxide under synthesis conditions. The contact solids used therein are disclosed as using a promoting amount of alkali metal, alkaline earth metal and/or compounds thereof. Thus, this patent also requires the presence of a reducible metal oxide, which reducible metal oxide may require periodic reoxidation to maintain the usefulness or efficiency of the contact solid for the conversion of methane.

SUMMARY OF THE INVENTION

It is an object of the present invention to overcome one or more of the problems described above.

According to the invention, a method for converting a feedstock alkane containing from 1 to 3 carbon atoms to a higher molecular weight hydrocarbon includes the step of contacting the feedstock with an oxygen-containing gas in the presence of a specific catalytic composition to produce a gaseous mixture including saturated and unsaturated aliphatic hydrocarbon products having higher molecular weights than the feedstock alkane from which they were formed.

This specified catalytic composition is effective in the catalytic conversion of the feedstock alkane to a higher molecular weight hydrocarbon. The composition includes a first component comprising a Group IA metal and a second component comprising a Group IIA metal, with the combination of the Group IA and the Group IIA metals being selected to be stable at oxidative coupling reaction conditions and with the Group IA metal of the first component and the Group IIA metal of the second component being in an atomic ratio of about 0.5:1 to about 2:1. The composition also includes a third component, the precursor of which includes a sol with which the first and second components are thoroughly dispersed. This sol includes an aqueous suspension of aluminum, silicon, titanium, zinc, zirconium, cadmium or tin. The third component makes up about 1 wt. % to about 30 wt. % of the composition.

The contacting of the feedstock with the oxygen-containing gas in the presence of the specified catalytic composition generally occurs in a temperature in the range of from about 600° C. to about 1000° C. and with the ratio of the combined feedstock alkane partial pressure to the oxygen partial pressure being in the range of from about 2:1 to about 40:1.

As used throughout this specification, the terms "reducible" metal and "reducible" metal oxides refer to those compounds which are reduced upon contacting methane at higher molecular weight hydrocarbon synthesizing conditions and include: one or more metal oxides such as those described by the general formula $M_xO_y$ where M is a metal, O is oxygen and the x and y subscription designate the atomic proportions of the metal and oxygen; and one or more oxygen-metal compounds having the capability and utility of resulting in higher hydrocarbon production upon the reduction thereof.

The term "activity" as used herein relative to catalytic compositions refers to the degree to which the catalytic material increases the reaction rate, e.g., the rate at which the material causes reaction to proceed to equilibrium.

The term "selectivity" as used herein relative to catalytic compositions refers to the fraction of reactant that is converted to a particular product, with mole percent selectivity being the mole ratio of products to reactants multiplied by 100.

As used herein, the term "sol" generally refers to aqueous colloidal solvent solutions.

In addition, the terms oxidative coupling "catalytic composition," "catalyst," and "catalyst composition" or the like as used herein do not have their standard meaning as while a relatively small amount of the material may notably affect the rate of reaction, the material itself or at least a component thereof may be consumed or undergo a chemical reaction.

It is to be understood that references herein to a particular catalyst composition component or catalyst preparation material as "comprising," "having," "including," or the like a specific periodic table element or group of elements refers to that component or material, as the case may be, as including such element or group of elements in either a compound or an elemental form.

Other objects and advantages of the invention will be apparent to those skilled in the art from the following detailed description, taken in conjunction with the appended claims and drawing.

BRIEF DESCRIPTION OF THE DRAWING

The FIGURE is a simplified schematic diagram of a preferred embodiment of the present invention.

It should be understood that the drawing is a schematic illustration, and that in certain instances, details which are not necessary for an understanding of the present invention but which render other details difficult to perceive may have been omitted. It should be understood, of course, that the invention is not necessarily limited to the particular embodiments illustrated herein.

DETAILED DESCRIPTION OF THE INVENTION

According to the invention, a method for converting lower alkanes to higher molecular weight hydrocarbons is provided. The invention contemplates a method of alkane conversion generally applicable to alkanes containing from 1 to 3 carbon atoms. It is to be understood, however, that while the method may also be utilized with higher alkane feedstocks, such use may, as a result of competing reaction kinetics, result in a reduction in the amount of higher molecular weight hydrocarbons formed thereby.

Referring to the FIGURE, a schematic of a system, generally designated 10, useful in the conversion of lower alkanes, i.e., lower molecular weight alkanes, e.g., methane, ethane and propane, to higher molecular weight hydrocarbons is shown. Methane, illustrative of a feedstock comprising at least one alkane containing from 1 to 3 carbon atoms is mixed with air, as a source of oxygen, and the resulting mixture is introduced through line 12 into a reactor 14 wherein the methane and air mixture is contacted with a suitable catalytic composition, as described below, for the oxidative coupling of the aforesaid alkane. It is to be understood, however, that alternative sources or forms of oxygen-containing gas may be used or preferred in the practice of the invention. Thus, the oxygen-containing gas for use in the method of this invention can vary in molecular oxygen content from oxygen-depleted air to air to oxygen gas itself, for example. Air or enriched air may be a preferred source of molecular oxygen. The oxygen-containing gas should provide a gas-vapor effluent mixture from the oxidative coupling reactor containing (measured on a solid-free basis) from about 2 to about 8 volume percent of oxygen, in order to avoid the flammability limits in such mixtures.

The effluent 16 from the reactor 14 is a gaseous mixture comprising carbon monoxide, carbon dioxide, nitrogen, any remaining unreacted feedstock alkane and oxygen, ethane and ethylene, illustrative of saturated and unsaturated aliphatic hydrocarbon products having higher molecular weights than the feedstock alkanes from they were formed, and may contain some traces of aromatics or higher hydrocarbons which may form in the reactor, such as at high operating temperatures, for example, at temperatures greater than about 750° C.

The effluent 16 from the oxidative coupling reactor 14 may illustratively be used as chemical feedstock or for subsequent conversion to gasoline-type products. For example, the effluent with desired or required pretreatment, e.g. $H_2O$ removal, and/or downstream treatment, e.g. $N_2$ removal, may be passed over a suitable aromatization/oligomerization catalyst to produce gasoline type products. Other specific uses of the reactor effluent will be apparent to those skilled in the art.

It should be understood that the FIGURE illustrates merely one preferred embodiment of the method of this invention and that the present invention is not limited to the particular embodiment illustrated in the FIGURE.

In the illustrated embodiment, methane and oxygen (as a part of air) are simultaneously contacted with the catalytic composition, commonly referred to as "co-feed" operation. Therefore, oxygen, which may be needed for the coupling reaction to occur, may be obtained directly from air, without the need for the oxygen to go through an intermediary such as may be required when oxygen is obtained from the lattice of an oxidative coupling catalyst composition. Further, co-feed operation may minimize or eliminate the need for subsequent regeneration of the catalytic material such as may be required to resupply lattice oxygen to catalytic materials such as those which typically contain reducible metal oxides as may occur when operated in a redox mode.

Generally, a suitable feedstock for the method of this invention comprises at least one of methane, ethane and propane and preferably comprises methane. Thus, a suitable feedstock for the method of this invention comprises natural gas, gases formed during mining operations and petroleum processes or in the above- or below-ground gasification or liquefaction of coal, tar sands, oil shale and biomass, for example.

The contacting of the feedstock with the oxygen-containing gas in the presence of the catalytic composition generally is performed at oxidative coupling reaction conditions including temperature and pressure. Preferably, such contacting is performed at a temperature in the range of from about 600° C. to about 1000° C, and, more preferably, in the range of from about 650° C. to about 850° C. These temperature ranges have been found to be preferred as operation at temperatures below about 600° C. may generally result in the catalytic compositions having relatively unfavorable selectivities while operation at higher temperatures, e.g., temperatures greater than about 900° C., may result in thermal reactions seriously competing with coupling reactions, with thermal reactions generally overwhelming coupling reactions at temperatures greater than about 1000° C. It is to be understood, however, that at higher reaction temperatures at least trace quantities of aromatics may also form.

Such contacting is preferably performed under a total absolute pressure in the range of from about 1 atmosphere to about 10 atmospheres, and more preferably in the range of from about 1 atmosphere to about 5 atmospheres. The ratio of the combined partial pressures of the feedstock alkanes containing from 1 to 3 carbon atoms and the feedstock to oxygen partial pressure at the entrance of the reactor in the contacting step is preferably in the range of from about 2:1 to about 40:1 and, more preferably, in the range of from about 2:1 to about 10:1. The combined partial pressures of the alkanes in the feedstock containing from 1 to 3 carbon atoms at the entrance to the reactor (the contacting reactor) is preferably no more than about 10 atmospheres, and, more preferably, no more than about 4 atmospheres. The oxygen partial pressure at the entrance to the reactor is preferably no more than about 4 atmospheres and, more preferably, no more than about 2 atmospheres. The oxygen partial pressure of the gaseous effluent from the reactor in the contacting step is preferably near 0 atmospheres.

The contacting step is preferably performed at a space velocity of from about 100 to about 20,000 volumes of total feed gas per volume of catalytic composition per hour and more preferably at a space velocity of about 800 to about 8000 volumes of total feed gas per volume of catalytic composition per hour.

The catalytic composition useful in the practice of the invention preferably contains a first component including a Group IA metal, such as lithium, sodium, potassium, rubidium or cesium and, preferably, is a Group IA metal, such as lithium, sodium or potassium, for example, in an oxygen-including form, e.g., an oxide.

The catalytic composition also preferably contains a second component including a Group IIA metal, such as beryllium, magnesium, calcium, strontium and barium and, more preferably, is a Group IIA metal such as those aforementioned, in an oxygen-including form, e.g., an oxide. In the practice of the invention, the utility of all Group IA and Group IIA metal combinations is not, at this time, believed to be universal. For example, as shown in Examples 2 and 3, below, the combinations of lithium with barium and sodium with barium, with each such combination also having a preferred form of the third component of such catalytic compositions, result in materials that are considered unstable at oxidative coupling reaction conditions, e.g., at oxidative coupling reaction temperatures and pressures these materials tend to revert to a form of a molten syrup as opposed to a dry solid. The selection of specific combinations of Group IA and Group IIA metals for incorporation in the catalytic compositions for use in the practice of the invention can be determined empirically by one skilled in the art guided by the teachings set forth herein. Useful specific combinations of Group IA and Group IIA metals for incorporation in the catalytic compositions for use in the practice of the invention may include combinations where: (a) the Group IA metal is sodium and the Group IIA metal is calcium or strontium or (b) the Group IA metal is potassium and the Group IIA metal is calcium, strontium or barium. Also, the Group IIA metal of the second component preferably has an ionic radius similar to that of the Group IA metal of the first component of the catalytic composition.

The ratio of the first and second components is believed important. Preferably, the catalytic composition includes the Group IA metal of the first component and the Group IIA metal component of the second component in an atomic ratio of about 0.5:1 to about 2:1 and, more preferably, about 0.8:1 to about 1.2:1 as compositions having ratios outside this range tended to have a larger degree of instability at oxidative coupling reaction conditions, with a ratio of about 1:1 being especially preferred.

The catalytic composition also preferably contains a third component which:

(a) increases the surface area of the catalytic composition, (b) serves as a medium for the substantially uniform and even dispersion of the above-described first and second components on the molecular scale and (c) increases the catalytic activity of the catalytic composition while maintaining its selectivity for the conversion of the feedstock alkane to hydrocarbon products having higher molecular weights than the feedstock alkane from which they were formed.

A precursor of the third component preferably includes, and more preferably is, an aqueous suspension of a metal such as aluminum, silicon, titanium, zinc, zirconium, cadmium and tin, for example, which, unlike conventional support materials, e.g. gamma alumina, silica or titania, on which the balance of the composition may form a type of surface coating, serves as a medium for the substantially uniform and even dispersion for the balance of the composition on a molecular scale. Preferably, such a precursor is a sol of at least one of the above-identified metals. More preferably, the third component of the catalytic composition is a silica or alumina sol, such as, PHF alumina sol, sold by American Cyanamid Co.

The effective use of such sols in the practice of the invention is generally believed to be independent of the aggregate size and concentration of the sol used provided that the balance of the composition is well dispersed, on a molecular scale, therewith. For example, it is to be generally understood that smaller volumes of a sol will be preferred when a more concentrated sol is used while a greater volume of sol will be preferred when a more dilute sol is used.

Preferably, the resulting catalytic composition will include at least about 1 weight percent to no more than about 30 weight percent and, more preferably, about 10 weight percent to about 20 weight percent of the third component, e.g., when the precursor of the third component is an alumina sol, the resulting catalytic composition will include at least about 1 weight percent to no more than 30 weight percent alumina expressed as $Al_2O_3$ and, more preferably, about 10 weight percent to about 20 weight percent alumina expressed as $Al_2O_3$.

Also, the catalytic compositions of the invention will typically have surface areas of less than about 25 $m^2$/gram and generally in the range of about 1 $m^2$/gram to about 25 $m^2$/gram and preferably in the range of about 1 $m^2$/gram to about 10 $m^2$/gram.

As will be further shown by the examples, such catalytic compositions can be prepared by a method involving:

(a) thoroughly dispersing in an aqueous medium a mixture including a first material (e.g., a precursor of the first component of the composition) including a Group IA metal, a second material (e.g., a precursor of the second component of the composition) including a Group IIA metal and a sol comprising an aqueous suspension of a metal such as aluminum, silicon, titanium, zinc, zirconium, cadmium or tin to form a slurry and (b) drying the slurry to evaporate substantially all of the water to leave behind a substantially dry solid material.

In such a method, the Group IA metal of the first material, the Group IIA metal of the second material and the metal of the sol are selected and in amounts and ratios to result in catalytic compositions effective in the conversion of a feedstock alkane containing from 1 to 3 carbon atoms to a higher molecular weight hydrocarbon, as described above.

The following examples illustrate the practice of the invention. It is to be understood that all changes that come within the spirit of the invention are desired to be protected and thus the invention is not to be construed as limited by these examples. Further, the compositions of the examples have been identified by a first component metal, a second component metal, a third component metal (with an indication if a sol precursor was used) or combinations thereof present in the particular composition being considered rather than the specific chemical state or form of the catalytic composition as various states or forms are believed possible and may be present as the preparations seek to come to equilibrium at various reaction conditions.

EXAMPLES

Reactor System

Ultra high purity methane and synthetic air were delivered in quantities to result in the specified ratios of $CH_4/O_2$ via Brooks Mass Flow Controllers and then mixed through a static mixer. The mixed feed was then delivered to the top of a fixed bed downflow tubular quartz reactor having a 14 mm inside diameter. A bed, 1-2 inches in length and containing the specified catalytic composition, was supported by a glass wool plug resting on concentric tube spacers in the lower part of the reactor. A 4 mm OD thermowell protruded through the center of the catalyst bed. Three thermocouples were inserted in the thermowell and positioned at the top, middle, and bottom of the catalyst bed. The reactor was heated in a split tube furnace. Effluent from the reactor was passed through a water trap, to a wet test meter for flow monitoring. Gas sampling was done via a gas tight syringe inserted into septa installed in the feed and effluent lines. Gas samples were injected into a gas chromatograph for analysis.

Experimental Procedure

The reactor containing the specified catalytic composition was purged in a flow of $N_2$ and brought up to about 400° C. Feed gas was then introduced. After a period of time sufficient to allow equilibration of the system, usually 10-20 minutes, a gas effluent sample was taken for analysis. The reactor was then heated to the next higher temperature, usually in 50°-100° C. intervals, allowed to equilibrate 10-20 minutes, and sampled again. The temperature ramping and gas sampling were continued on up to the maximum desired temperature, usually not higher than 850° C. Analyses of the reactor effluents were compared to the analysis of the feed gas composition and conversions and selectivities were calculated.

Calculation of Conversions and Selectivities

The feed gas composition, containing only methane, nitrogen, and oxygen, was normalized to 100 moles of methane. Since nitrogen was used as an internal standard and undergoes no reaction in the system, the effluent concentrations were multiplied by a factor such that the nitrogen amount was the same as in the normalized feed composition. Conversion of methane was then calculated by:

methane conversion=(mole of methane in feed—moles of methane in effluent)×100.

The amounts of each of the products from the adjusted effluent concentrations were multiplied by the number of carbon atoms in the respective product. Summing these amounts then gave a second measure for methane conversion which could be compared to the first measure as an indication of mass balance. Typical mass balances for an equilibrated system at high conversions were in the region of 98-102% correspondence. Selectivities of each of the products were calculated by dividing the respective adjusted effluent concentrations (multiplied by the carbon number) by the sum of these amounts.

Example 1—Li/Mg/Al(sol)

The following is a general description of the method of preparation of Li/Mg/Al(sol) catalytic compositions, according to the invention. In certain instances, the quantities of reagents used were adjusted to give desired Li/Mg or Li/Mg/Al ratios.

About 173 g of PHF alumina sol (10.7% solids) and 150 ml of distilled water were thoroughly mixed in a blender. About 20 g MgO and 18.9 g of $LiOH.H_2O$ in 200 ml $H_2O$ were added to the alumina solution and the mixture was blended until it became a thick, slurry-type of material. This slurry mixture was then dried overnight in a vacuum oven at about 100° C. The dried composition was then calcined for about 3 hours in a muffle furnace at about 750° C., and then crushed and screened to about 14–60 mesh. The dried, calcined material had a calculated elemental analysis of: 6.3 wt. % Li, 24.5 wt. % Mg and 18.8 wt. % Al (with weight percents as metals), with the balance of the composition being oxygen (as oxides or hydroxides, for example).

Data with respect to the evaluation of the compositions for the oxidative coupling of methane is presented in Tables I-XII. Unless otherwise indicated, the ratio of Li/Mg is to be taken as about 1.

Example 2—Li/Ba/Al(sol)

In a blender, about 50 g of $LiOH.H_2O$ and 223 g of $Ba(OH)_2.8H_2O$ were mixed in 200 ml $H_2O$. To the mixture was added about 50 ml $H_2O$ and 235 g PHF alumina (about 7.67 wt. % solvent) and blended thoroughly therewith. The mixture was then dried in a vacuum oven and crushed and screened to about 14–60 mesh. The dried, crushed, screened composition was then $CO_2$ treated at about 50 cc/min. for about 3 hours and then calcined at about 700° C. for about 2 hours. The dried, calcined material had a calculated elemental analysis of: 5.3 wt. % Li, 69.9 wt. % Ba and 11.6 wt. % Al (with weight percents as metals), with the balance of the composition being oxygen (as oxides or hydroxides, for example).

Note: The first attempt to run this composition without $CO_2$ treatment and calcination resulted in the preparation melting and shrinking to about one-third of its original size. A second portion of the preparation was $CO_2$ treated (no exotherm noted) and calcined but melted during the calcining procedure.

The Li/Ba/Al(sol) composition proved unstable at oxidative coupling reaction conditions and no data could be obtained.

Example 3—Na/Ba/Al(sol)

About 473 g of NaOH and 223 g of $Ba(OH)_2.8H_2O$ were mixed with about 200 ml $H_2O$ in a blender. A mixture of about 235 g of PHF alumina sol (about 7.67 wt. % solids) and about 100 ml of $H_2O$ was added to the mixture and the blending was continued. The mixture was then dried in a vacuum oven, crushed and screened to about 14–60 mesh. The dried, crushed, screened composition was then $CO_2$ treated until exotherm was completed and then calcined at about 700° C. for about 2 hours. The dried, calcined material had a calculated elemental analysis of: 15.7 wt. % Na, 55.9 wt. % Ba and 5.2 wt. % Al (with weight percents as metals), with the balance of the composition being oxygen (as oxides or hydroxides, for example).

The Na/Ba/Al(sol) composition proved unstable at oxidative coupling reaction conditions and no data could be obtained.

Example 4—K/Ba/Al(sol)

In a blender, about 234.7 g of PHF alumina (about 7.67 wt. % solid) and 222.8 g of $BA(OH)_2.8H_2O$ in 100 ml of $H_2O$ were mixed. To the mixture was added a solution of about 69.8 g of KOH in about 65 ml of $H_2O$ and blended thoroughly therewith. The mixture was then dried in a vacuum oven and crushed and screened to about 14–60 mesh. The dried, crushed, screened composition was then $CO_2$ treated at about 50 cc/min. for about 3 hours and then calcined at about 700° C. for about 2 hours. The dried, calcined material had a calculated elemental analysis of: 23.5 wt. % K, 49.5 wt. % Ba and 4.6 wt. % Al (with weight percents as metals), with the balance of the composition being oxygen (as oxides or hydroxides, for example).

Data with respect to the evaluation of this composition for the oxidative coupling of methane is presented in Table XIII.

Example 5—Ca/Li/Al(sol)

About 181 g of PHF alumina sol (about 9.93 wt. % solids) was mixed in a blender with about 100 ml of distilled water. About 49.6 g of LiOH and 73 g of CaO were dissolved in a beaker with about 400 ml of distilled water. The resultant slurry was then added to the alumina sol solution in the blender and mixed thoroughly. The resultant preparation was dried overnight at about 100° C. in a vacuum oven. The dried composition was crushed and screened to about 14–60 mesh. The dried, calcined material had a calculated elemental analysis of: 6.9 wt. % Li, 43.7 wt. % Ca and 7.5 wt. % Al (with weight percents as metals), with the balance of the composition being oxygen (as oxides or hydroxides, for example).

Data with respect to the evaluation of this composition for the oxidative coupling of methane is presented in Table XIV.

Example 6—Li/Mg/Si(sol)

About 11.8 g of NALCOAG silica ($SiO_2$) sol (34% $SiO_2$) was mixed with about 50 ml of water in a blender. A slurry of about 10.48 g of MgO and about 9.92 g of $LiOH.H_2O$ in about 80 ml of $H_2$ was added to the blender and thoroughly mixed. Subsequently, about 30 ml of a saturated solution of $(NH_4)_2CO_3$ solution was added to the blender and blended in. The resultant slurry was dried in a vacuum oven and calcined for about 3 hours at about 750° C. The calcined material was crushed and screened to about 14–60 mesh. The dried, calcined material had a calculated elemental analysis of: 8.1 wt. % Li, 31.4 wt. % Mg and 9.3 wt. % Si (with weight percents as metals), with the balance of the composition being oxygen (as oxides or hydroxides, for example).

Data with respect to the evaluation of this composition for the oxidative coupling of methane is presented in Table XVI.

Comparative Example 1—Mg

A paste was prepared from about 50 g MgO powder (Baker 95.5 wt. % MgO) and 100 ml distilled $H_2O$. The paste was then dried overnight in a vacuum oven at about 100° C. The dried material was then crushed and screened to about 14–60 mesh. The crushed and screened material was charged to the reactor and then calcined in situ at about 450° C. in air for about 1½ hours.

Data with respect to the evaluation of this composition for the oxidative coupling of methane is presented in Table XVII.

Comparative Example 2—Li/Mg

About 19 g of $LiOH.H_2O$ was dissolved in about 90 ml of distilled $H_2O$. About 20 g of MgO powder was added to the solution to make a thick slurry. The slurry was then dried overnight in a vaccum oven at about 100° C. The dried material was crushed and screened to about 14-60 mesh. The crushed and screened material was charged to the reactor and then calcined in situ at about 450° C. in air for about 1½ hours. The dried, calcined material had a calculated elemental analysis of: 10.2 wt. % Li and 39.1 wt. % Mg (with weight percents as metals), with the balance of the composition being oxygen (as oxides or hydroxides, for example).

Data with respect to the evaluation of this composition for the oxidative coupling of methane is presented in Table XVIII.

Comparative Example 3—Li/Mg/Si

A composition preparation similar to that of Example 1, described above, was prepared except that Norton $SiO_2$ (Type 16843) was substituted for the PHF alumina sol in the preparation. The amount of $SiO_2$ used was adjusted to give about 15 wt. % $SiO_2$ in the dried, crushed, screened and calcined composition. The dried, calcined material had a calculated elemental analysis of: 8.6 wt. % Li, 33.3 wt. % Mg and 7.0 wt. % Si (with weight percents as metals), with the balance of the composition being oxygen (as oxides or hydroxides, for example).

Data with respect to the evaluation of this composition for the oxidative coupling of methane is presented in Table XIX.

DISCUSSION OF EXAMPLES

As shown in Table I, the catalytic composition identified as Li/Mg/Al(sol) had a selectivity to $C_{2+}$ of greater than 84 mole percent in the temperature of 730°-780° C. Low feed $CH_4/O_2$ mole ratios, e.g., $CH_4/O_2$ mole ratios <2, were not conducive to oxidative coupling of methane but rather lead to the production of syngas, i.e., a mixture of $H_2$ and CO, as shown in Table II. Tables III and IV show that when the $CH_4/O_2$ ratio was changed from 1.6/1 to about 21.5/1 and the space velocity was varied from 150 to 563 $hr^{-1}$, substantially complete conversion of $O_2$ was obtained in the temperature range of about 600°-650° C. and selectivities to $C_{2+}$ as high as 78% were obtained. Note that the selectivity to CO is high at low temperature (approximately 500°), but decreases to about 0 at intermediate temperatures and then increases again at higher temperatures. Tables V-VIII show the effected temperatures, $CH_4/O_2$ ratio and space velocity on selectivity to $C_{2+}$ for this composition.

Tables IX and X illustrate the effect of varying the amount of alumina, expressed as $Al_2O_3$, in the catalytic composition. Thus, while the incorporation of greater amounts of $Al_2O_3$ in the catalytic composition resulted in a composition with increased catalytic activity, the selectivity of the composition to $C_{2+}$ decreased significantly as the amount of $Al_2O_3$ was increased. Thus, a composition with about 15 wt. % alumina expressed as $Al_2O_3$ gave superior selectivity performance relative to a composition comprising 70 wt. % alumina expressed as $Al_2O_3$.

Tables XI and XII illustrate that compositions with a Li/Mg ratio of about 1.2 were found to result in poorer selectivity performance, as compared to similar compositions but with a Li/Mg ratio of about 1, at similar conditions. These compositions also evidenced some catalytic composition instability.

Tables XIII and XIV present data for catalytic composition comprising different Group IA and/or Group IIA components. Table XIII presents data relative to the evaluation of the composition K/Ba/Al(sol). Table XIII shows that a maximum selectivity to $C_{2+}$ of about 69.5 mole percent was obtained at a temperature of around 735° C. Table XIV shows that a selectivity to $C_{2+}$ of greater than 94% was obtained for the composition Li/Ca/Al(sol) at a temperature of about 690° C. Thus, while the K/Ba/Al(sol) composition had a comparatively lower maximum selectivity to $C_{2+}$ than the Li/Mg/Al(sol) of earlier tables with similar wt. % of alumina expressed as $Al_2O_3$ at comparable conditions, the Li/Ca/Al(sol) composition had a comparatively higher maximum selectivity than the "base" Li/Mg/Al(sol) composition.

Tables XV and XVI present data relative to compositions wherein silica sol was used rather than alumina sol. The significance of using a third component which increases the surface area of the catalytic composition and serves as a medium for the substantially uniform and even dispersion of the other components of the composition on a molecular scale is illustrated when the selectivities obtained with compositions prepared with silica sol are compared with the results obtained with a similar composition but wherein standard silica solid, such as Norton $SiO_2$ (Type 16843), is used as shown in Table XVII. These results show that substantially higher selectivities to $C_{2+}$ were obtained when the sol form was used as opposed to standard silica solid.

In addition, Tables XVIII and XIX present selectivity and conversion data for compositions comprising a Group IIA metal (Mg) but no Group IA metal or the specified third component and a combination of a Group IA metal and a Group IIA metal (Li/Mg) but no specified third component, respectively. In both instances, selectivities to $C_{2+}$ significantly below the catalytic composition disclosed herein were obtained.

The foregoing detailed description is given for clearness of understanding only, and no unnecessary limitations are to be understood therefrom, as modifications within the scope of the invention will be obvious to those skilled in the art.

TABLE I

| | Li/Mg/Al(sol) (30% alumina) | | | | | | | | |
|---|---|---|---|---|---|---|---|---|---|
| | Run | | | | | | | | |
| | 42 | 43 | 44 | 45 | 47 | 48 | 49 | 50 | 51 |
| Temp. °C. (avg.) | 496 | 530 | 580 | 584 | 638 | 683 | 734 | 783 | 833 |
| SV (hr−1) | 1215 | 1215 | 1215 | 1215 | 1215 | 1215 | 1215 | 1215 | 1215 |
| CH4/O2 mole ratio | 20.4 | 20.4 | 20.4 | 20.9 | 20.9 | 20.9 | 20.9 | 20.9 | 20.9 |
| O2/CH4 mole ratio | .0490 | .0490 | .0490 | .0479 | .0479 | .0479 | .0479 | .0479 | .0479 |
| Conv. of Oxygen, mole % | 9.0 | 22.6 | 65.6 | 69.8 | 97.0 | 99.3 | 99.3 | 99.4 | 99.4 |
| Conv. of CH4, mole % (1) | 0.3 | 0.9 | 3.2 | 3.5 | 6.6 | 8.1 | 9.0 | 9.0 | 8.6 |
| Residence Time, sec. | .421 | .403 | .380 | .378 | .355 | .339 | .321 | .307 | .293 |
| Selectivity, mole % | | | | | | | | | |
| H2 | — | — | 49.3 | 46.2 | 17.8 | — | — | — | 17.4 |
| CO | 47.8 | 44.6 | 27.7 | 25.3 | 5.9 | 1.3 | 0.9 | 0.7 | 5.6 |
| CO2 | 52.2 | 51.9 | 47.7 | 46.5 | 29.3 | 18.2 | 14.2 | 15.1 | 18.5 |

TABLE I-continued

Li/Mg/Al(sol) (30% alumina)

| | Run | | | | | | | | |
|---|---|---|---|---|---|---|---|---|---|
| | 42 | 43 | 44 | 45 | 47 | 48 | 49 | 50 | 51 |
| C2H4 | — | — | 2.1 | 2.4 | 13.7 | 23.7 | 27.9 | 31.1 | 34.1 |
| C2H6 | — | 3.5 | 22.1 | 25.2 | 47.2 | 51.0 | 51.4 | 48.1 | 36.9 |
| C2H2 | — | — | — | — | — | — | — | — | — |
| C3H8 & C3H6 | — | — | 0.4 | 0.5 | 3.9 | 5.2 | 4.8 | 4.2 | 3.9 |
| i-C4= | — | — | — | — | — | 0.7 | 0.5 | 0.6 | 0.8 |
| l-C4 | — | — | — | — | — | — | — | — | — |
| n-C4 | — | — | — | — | — | — | 0.3 | 0.3 | 0.2 |
| Unk (C4) | — | — | — | — | — | — | — | — | — |
| Unk (C5) | — | — | — | — | — | — | — | — | — |
| Unk (C6) | — | — | — | — | — | — | — | — | — |
| Sel. to C2+, mole % | 0 | 3.5 | 24.6 | 28.1 | 64.8 | 80.6 | 84.9 | 84.3 | 75.9 |
| C2H4/C2H6 | — | 0 | .097 | .095 | .290 | .465 | .542 | .647 | .919 |
| H2/CO | 0 | 0 | 3.221 | 1.824 | 3.532 | 0 | 0 | 0 | 3.09 |
| CO/CO2 | .913 | .859 | .580 | .545 | .252 | .069 | .065 | .049 | .304 |

TABLE II

Li/Mg/Al(sol) (30% alumina)

| | Run | | | | | | | | |
|---|---|---|---|---|---|---|---|---|---|
| | 3 | 4 | 5 | 6 | 8 | 9 | 10 | 11 | 12 |
| Temp. °C. (avg.) | 422 | 471 | 528 | 614 | 618 | 671 | 706 | 762 | 813 |
| SV (hr−1) | 161 | 161 | 161 | 161 | 161 | 161 | 161 | 161 | 161 |
| CH4/O2 mole ratio | 1.60 | 1.60 | 1.60 | 1.60 | 1.52 | 1.52 | 1.52 | 1.52 | 1.52 |
| O2/CH4 mole ratio | 0.626 | 0.626 | 0.626 | 0.626 | 0.657 | 0.657 | 0.657 | 0.657 | 0.657 |
| Conv. of Oxygen, mole % | 3.0 | 11.3 | 45.6 | 96.2 | 95.9 | 99.4 | 99.4 | 99.4 | 99.4 |
| Conv. of CH4, mole % (1) | 1.1 | 4.5 | 20.2 | 42.3 | 38.8 | 41.7 | 55.6 | 58.5 | 44.9 |
| Residence Time, sec. | 3.52 | 3.28 | 3.05 | 2.76 | 2.74 | 2.59 | 2.50 | 2.36 | 2.25 |
| Selectivity, mole % | | | | | | | | | |
| H2 | — | — | 79.4 | — | — | — | — | — | — |
| CO | — | — | 10.4 | 3.4 | 0 | 0.2 | 1.4 | 3.2 | 3.9 |
| CO2 | 100 | 100 | 88.9 | 82.9 | 84.0 | 71.3 | 76.3 | 80.5 | 84.7 |
| C2H4 | — | — | — | 6.6 | 7.9 | 16.2 | 13.3 | 11.0 | 7.9 |
| C2H6 | — | — | 0.7 | 6.6 | 7.5 | 11.3 | 8.2 | 5.0 | 3.3 |
| C2H2 | — | — | — | — | — | — | — | — | — |
| C3H8 & C3H6 | — | — | — | 0.5 | 0.6 | 1.1 | 0.8 | 0.3 | 0.2 |
| i-C4= | — | — | — | — | — | — | — | — | — |
| l-C4 | — | — | — | — | — | — | — | — | — |
| n-C4 | — | — | — | — | — | — | — | — | — |
| Unk (C4) | — | — | — | — | — | — | — | — | — |
| Unk (C5) | — | — | — | — | — | — | — | — | — |
| Unk (C6) | — | — | — | — | — | — | — | — | — |
| Sel. to C2+, mole % | 0 | 0 | 0.7 | 13.7 | 16.0 | 28.6 | 22.3 | 16.3 | 11.4 |
| C2H4/C2H6 | — | — | 0 | 0.991 | 1.044 | 1.432 | 1.618 | 2.186 | 2.439 |
| H2/CO | — | — | 7.614 | 0 | 0 | 0 | 0 | 0 | 0 |
| CO/CO2 | 0 | 0 | .117 | .041 | 0 | .003 | .018 | .039 | .046 |

TABLE III

Li/Mg/Al(sol) (30% alumina)

| | Run | | | | | | |
|---|---|---|---|---|---|---|---|
| | 14 | 15 | 16 | 17 | 18 | 19 | 20 |
| Temp. °C. (avg.) | 502 | 501 | 553 | 601 | 655 | 670 | 766 |
| SV (hr−1) | 250 | 150 | 150 | 150 | 150 | 150 | 150 |
| CH4/O2 mole ratio | 21.5 | 21.5 | 21.5 | 21.5 | 21.5 | 21.5 | 21.5 |
| O2/CH4 mole ratio | 0.0465 | 0.0465 | 0.0465 | 0.0465 | 0.0465 | 0.0465 | 0.0465 |
| Conv. of Oxygen, mole % | 68.4 | 31.5 | 90.8 | 99.3 | 99.3 | 99.3 | 99.3 |
| Conv. of CH4, mole % (1) | 0 | 0.8 | 2.5 | 3.8 | 5.8 | 6.7 | 6.4 |
| Residence Time, sec. | 3.38 | 3.38 | 3.17 | 3.00 | 2.82 | 2.78 | 2.52 |
| Selectivity, mole % | | | | | | | |
| H2 | (4) | 0 | 0 | — | — | — | — |
| CO | (4) | 22.9 | 1.06 | — | — | — | 2.9 |
| CO2 | (4) | 77.1 | 76.6 | 51.9 | 27.9 | 28.7 | 43.3 |
| C2H4 | (4) | — | 1.1 | 8.9 | 21.9 | 26.4 | 28.4 |
| C2H6 | (4) | — | 11.7 | 37.4 | 45.0 | 40.4 | 20.3 |
| C2H2 | (4) | — | — | — | — | — | — |
| C3H8 & C3H6 | (4) | — | — | 1.8 | 3.4 | 3.1 | 3.6 |
| i-C4= | (4) | — | — | — | 1.2 | 0.4 | 0.9 |
| l-C4 | (4) | — | — | — | — | — | — |
| n-C4 | (4) | — | — | — | 0.6 | 1.0 | 0.6 |
| Unk (C4) | (4) | — | — | — | — | — | — |
| Unk (C5) | (4) | — | — | — | — | — | — |
| Unk (C6) | — | — | — | — | — | — | — |
| Sel. to C2+, mole % | (4) | 0 | 1.28 | 48.1 | 72.1 | 71.3 | 53.8 |
| C2H4/C2H6 | (4) | — | .094 | .239 | .487 | .654 | 1.401 |

TABLE III-continued

| | Li/Mg/Al(sol) (30% alumina) | | | | | | |
|---|---|---|---|---|---|---|---|
| | Run | | | | | | |
| | 14 | 15 | 16 | 17 | 18 | 19 | 20 |
| H2/CO | (4) | 0 | 0 | 0 | — | — | 0 |
| CO/CO2 | (4) | .297 | 1.39 | 0 | 0 | 0 | .066 |

TABLE IV

| | Li/Mg/Al(sol) (30% alumina) | | | | | | | | |
|---|---|---|---|---|---|---|---|---|---|
| | Run | | | | | | | | |
| | 22 | 23 | 24 | 25 | 26 | 27 | 29 | 30 | 31 |
| Temp. °C. (avg.) | 536 | 569 | 614 | 672 | 714 | 766 | 549 | 605 | 661 |
| SV (hr−1) | 298 | 298 | 298 | 298 | 298 | 298 | 563 | 563 | 563 |
| CH4/O2 mole ratio | 21.3 | 21.3 | 21.3 | 21.3 | 21.3 | 21.3 | 21.3 | 21.3 | 21.3 |
| O2/CH4 mole ratio | .0471 | .0471 | .0471 | .0471 | .0471 | .0471 | .0469 | .0469 | .0469 |
| Conv. of Oxygen, mole % | 43.7 | 82.7 | 99.3 | 99.3 | 99.3 | 99.3 | 43.5 | 93.1 | 99.3 |
| Conv. of CH4, mole % (1) | 1.3 | 2.7 | 3.8 | 6.1 | 6.6 | 7.4 | 0.5 | 3.6 | 5.7 |
| Residence Time, sec. | 1.63 | 1.57 | 1.49 | 1.40 | 1.34 | 1.27 | 0.850 | 1.796 | .749 |
| Selectivity, mole % | | | | | | | | | |
| H2 | — | 38.5 | — | — | — | — | 193 | — | — |
| CO | 28.9 | 15.7 | 0.1 | — | — | 1.3 | 76.8 | 6.5 | — |
| CO2 | 68.2 | 73.2 | 54.2 | 28.1 | 22.5 | 37.3 | 3.3 | 57.7 | 30.2 |
| C2H4 | — | — | 6.7 | 18.8 | 24.0 | 26.8 | — | 3.8 | 14.0 |
| C2H6 | 2.9 | 11.1 | 36.0 | 48.1 | 49.1 | 30.3 | 20.0 | 30.2 | 51.1 |
| C2H2 | — | — | — | — | — | — | — | — | — |
| C3H8 & C3H6 | — | — | 1.4 | 3.5 | 3.3 | 2.6 | — | 0.8 | 3.4 |
| i-C4= | — | — | 1.7 | 1.0 | 0.6 | 1.1 | — | 1.0 | 1.3 |
| 1-C4 | — | — | — | — | — | — | — | — | — |
| n-C4 | — | — | — | 0.6 | 0.6 | 0.6 | — | — | — |
| Unk (C4) | — | — | — | — | — | — | — | — | — |
| Unk (C5) | — | — | — | — | — | — | — | — | — |
| Unk (C6) | — | — | — | — | — | — | — | — | — |
| Sel. to C2+, mole % | 2.9 | 11.1 | 45.8 | 72.0 | 77.6 | 61.4 | 20.0 | 35.8 | 69.8 |
| C2H4/C2H6 | 0 | 0 | .186 | .390 | .489 | .883 | 0 | .127 | .274 |
| H2/CO | 0 | 2.456 | 0 | 0 | 0 | 0 | 3.127 | 0 | 0 |
| CO/CO2 | .424 | .214 | .002 | 0 | 0 | .035 | 23.67 | .112 | 0 |

TABLE V

| | Li/Mg/Al(sol) (30% alumina) | | | | | | | |
|---|---|---|---|---|---|---|---|---|
| | Run | | | | | | | |
| | 33 | 34 | 35 | 37 | 37 | 38 | 39 | 40 |
| Temp. °C. (avg.) | 435 | 478 | 531 | 581 | 632 | 682 | 734 | 783 |
| SV (hr−1) | 563 | 563 | 563 | 563 | 563 | 563 | 563 | 563 |
| CH4/O2 mole ratio | 21.1 | 21.1 | 21.1 | 21.1 | 21.1 | 21.1 | 21.1 | 21.1 |
| O2/CH4 mole ratio | .0475 | .0475 | .0475 | .0475 | .0475 | .0475 | .0475 | .0475 |
| Conv. of Oxygen, mole % | 6.1 | 23.0 | 78.6 | 99.4 | 99.4 | 99.4 | 99.4 | 98.7 |
| Conv. of CH4, mole % (1) | 0.2 | 0.9 | 3.4 | 4.8 | 6.3 | 7.8 | 8.7 | 8.2 |
| Residence Time, sec. | .988 | .931 | .0869 | .819 | .773 | .732 | .694 | .662 |
| Selectivity, mole % | | | | | | | | |
| H2 | — | — | 76.6 | 55.3 | 20.1 | — | — | 13.9 |
| CO | 63.2 | 49.6 | 35.2 | 18.7 | 5.6 | 2.0 | 1.7 | 4.2 |
| CO2 | 36.8 | 50.4 | 62.7 | 54.9 | 34.6 | 23.6 | 19.6 | 21.6 |
| C2H4 | — | — | — | 3.2 | 13.7 | 22.8 | 28.8 | 32.6 |
| C2H6 | — | — | 2.1 | 22.5 | 42.4 | 47.1 | 44.6 | 36.6 |
| C2H2 | — | — | — | — | — | — | — | — |
| C3H8 & C3H6 | — | — | — | 0.8 | 3.0 | 4.1 | 4.2 | 4.2 |
| i-C4= | — | — | — | — | 0.6 | 0.3 | 0.4 | 0.5 |
| 1-C4 | — | — | — | — | — | — | 0.3 | — |
| n-C4 | — | — | — | — | — | — | 0.4 | 0.2 |
| Unk (C4) | — | — | — | — | — | — | — | — |
| Unk (C5) | — | — | — | — | — | — | — | — |
| Unk (C6) | — | — | — | — | — | — | — | — |
| Sel. to C2+, mole % | 0 | 0 | 2.1 | 26.5 | 59.7 | 74.3 | 78.7 | 74.1 |
| C2H4/C2H6 | — | — | 0 | .140 | .303 | .485 | .485 | .890 |
| H2/CO | 0 | 0 | 2.177 | 2.962 | 3.610 | 0 | 0 | 3.293 |
| CO/CO2 | 1.727 | .986 | .562 | .340 | .161 | .085 | .087 | .195 |

TABLE VI

| | Li/Mg/Al(sol) (30% alumina) | | | | | | | | | |
|---|---|---|---|---|---|---|---|---|---|---|
| | Run | | | | | | | | | |
| | 53 | 54 | 55 | 57 | 58 | 59 | 60 | 61 | 63 | 64 |
| Temp. °C. (avg.) | 507 | 585 | 636 | 647 | 684 | 733 | 784 | 833 | 463 | 578 |
| SV (hr−1) | 2318 | 2318 | 2318 | 2318 | 2318 | 2318 | 2318 | 2318 | 2175 | 2175 |

TABLE VI-continued

Li/Mg/Al(sol) (30% alumina)

| | Run | | | | | | | | | |
|---|---|---|---|---|---|---|---|---|---|---|
| | 53 | 54 | 55 | 57 | 58 | 59 | 60 | 61 | 63 | 64 |
| CH4/O2 mole ratio | 20.6 | 20.6 | 20.6 | 20.5 | 20.5 | 20.5 | 20.5 | 20.5 | 12.6 | 12.6 |
| O2/CH4 mole ratio | .0486 | .0486 | .0486 | .0487 | .0487 | .0487 | .0487 | .0487 | 0.791 | 0.791 |
| Conv. of Oxygen, mole % | 5.0 | 35.6 | 78.6 | 86.2 | 97.2 | 99.4 | 99.4 | 99.4 | 3.3 | 17.2 |
| Conv. of CH4, mole % (1) | — | 1.7 | 5.0 | 5.9 | 8.1 | 9.1 | 9.4 | 9.4 | 0 | 1.2 |
| Residence Time, sec. | .218 | .198 | .187 | .184 | .177 | .169 | .160 | .153 | .246 | .213 |
| Selectivity, mole % | | | | | | | | | | |
| H2 | (4) | 39.7 | 30.1 | 17.1 | — | — | 11.6 | 9.7 | (4) | — |
| CO | (4) | 33.9 | 13.1 | 7.4 | 1.7 | 0.4 | 1.6 | 3.3 | (4) | 40.5 |
| CO2 | (4) | 47.8 | 34.3 | 27.9 | 18.5 | 13.8 | 13.8 | 14.3 | (4) | 51.3 |
| C2H4 | (4) | — | 7.4 | 11.2 | 20.2 | 26.7 | 29.3 | 33.5 | (4) | — |
| C2H6 | (4) | 18.2 | 43.1 | 50.0 | 53.5 | 53.5 | 50.0 | 43.9 | (4) | 8.2 |
| C2H2 | (4) | — | — | — | — | — | — | — | (4) | — |
| C3H8 & C3H6 | (4) | — | 2.2 | 3.4 | 5.2 | 4.8 | 3.9 | 3.6 | (4) | — |
| i-C4= | (4) | — | — | — | 0.5 | 0.8 | 1.2 | 1.3 | (4) | — |
| 1-C4 | (4) | — | — | — | 0.4 | — | 0.1 | — | (4) | — |
| n-C4 | (4) | — | — | — | — | — | 0.2 | 0.2 | (4) | — |
| Unk (C4) | (4) | — | — | — | — | — | — | — | (4) | — |
| Unk (C5) | (4) | — | — | — | — | — | — | — | (4) | — |
| Unk (C6) | (4) | — | — | — | — | — | — | — | (4) | — |
| Sel. to C2+, mole % | (4) | 18.2 | 52.7 | 64.6 | 79.8 | 85.8 | 84.7 | 82.5 | (4) | 8.2 |
| C2H4/C2H6 | (4) | 0 | .171 | .224 | .378 | .498 | .584 | .763 | (4) | 0 |
| H2/CO | (4) | 1.170 | 2.301 | 2.311 | 0 | 0 | 7.024 | 2.956 | (4) | 0 |
| CO/CO2 | (4) | .710 | .381 | .265 | .094 | .029 | .119 | .231 | (4) | .790 |

TABLE VII

Li/Mg/Al(sol) (30% alumina)

| | Run | | | | | | | | | |
|---|---|---|---|---|---|---|---|---|---|---|
| | 65 | 66 | 67 | 68 | 70 | 71 | 73 | 74 | 75 | 76 |
| Temp. °C. (avg.) | 633 | 682 | 731 | 785 | 788 | 832 | 491 | 592 | 654 | 706 |
| SV (hr−1) | 2175 | 2175 | 2175 | 2175 | 2175 | 2175 | 4275 | 4275 | 4275 | 4275 |
| CH4/O2 mole ratio | 12.6 | 12.6 | 12.6 | 12.6 | 12.6 | 12.6 | 12.7 | 12.7 | 12.7 | 12.7 |
| O2/CH4 mole ratio | .0791 | .0791 | .0791 | .0791 | .0794 | .0794 | .0784 | .0784 | .0784 | .0784 |
| Conv. of Oxygen, mole % | 57.0 | 91.4 | 99.2 | 99.5 | 99.5 | 99.6 | 0.9 | 13.3 | 52.2 | 93.6 |
| Conv. of CH4, mole % (1) | 5.0 | 10.0 | 11.9 | 12.8 | 13.1 | 12.8 | 0 | 1.0 | 4.8 | 11.5 |
| Residence Time, sec. | .200 | .189 | .180 | .171 | .170 | .164 | .120 | .106 | .099 | .094 |
| Selectivity, mole % | | | | | | | | | | |
| H2 | 44.7 | 10.0 | — | 10.1 | 11.0 | 14.1 | (4) | — | 33.5 | — |
| CO | 19.2 | 4.1 | 1.7 | 2.4 | 2.5 | 4.2 | (4) | 40.9 | 17.3 | 1.7 |
| CO2 | 43.0 | 27.8 | 21.4 | 19.1 | 18.5 | 19.5 | (4) | 49.7 | 39.2 | 20.6 |
| C2H4 | 5.1 | 17.8 | 28.0 | 32.5 | 31.8 | 35.7 | (4) | — | 5.1 | 22.5 |
| C2H6 | 31.6 | 44.3 | 43.3 | 41.2 | 40.1 | 36.1 | (4) | 9.3 | 35.9 | 48.8 |
| C2H2 | — | — | — | — | — | — | (4) | — | — | — |
| C3H8 & C3H6 | 1.1 | 4.5 | 4.5 | 3.9 | 3.8 | 3.8 | (4) | — | 1.3 | 5.2 |
| i-C4= | — | 1.1 | 0.9 | 0.5 | 2.4 | 0.3 | (4) | — | 1.3 | 0.8 |
| 1-C4 | — | 0.3 | 0.3 | 0.1 | 0.4 | 0.4 | (4) | — | — | 0.4 |
| n-C4 | — | — | — | 0.3 | 0.4 | 0.4 | (4) | — | — | — |
| Unk (C4) | — | — | — | — | — | — | (4) | — | — | — |
| Unk (C5) | — | — | — | — | — | — | (4) | — | — | — |
| Unk (C6) | — | — | — | — | — | — | (4) | — | — | — |
| Sel. to C2+, mole % | 37.8 | 68.0 | 77.0 | 78.5 | 78.9 | 76.4 | (4) | 9.3 | 43.6 | 77.7 |
| C2H4/C2H6 | .162 | .403 | .646 | .789 | .794 | .988 | (4) | 0 | .142 | .462 |
| H2/CO | 2.328 | 2.418 | 0 | 4.167 | 4.361 | 3.452 | (4) | 0 | 1.937 | 0 |
| CO/CO2 | .446 | .148 | .080 | .127 | .136 | .214 | (4) | .822 | .441 | .082 |

TABLE VIII

Li/Mg/Al(sol) (30% alumina)

| | Run | | | | | | | | | |
|---|---|---|---|---|---|---|---|---|---|---|
| | 77 | 78 | 79 | 81 | 82 | 83 | 84 | 85 | 86 | 87 |
| Temp. °C. (avg.) | 749 | 797 | 846 | 520 | 582 | 632 | 688 | 737 | 784 | 833 |
| SV (hr−1) | 4275 | 4275 | 4275 | 1286 | 1286 | 1286 | 1286 | 1286 | 1286 | 1286 |
| CH4/O2 mole ratio | 12.7 | 12.7 | 12.7 | 6.63 | 6.63 | 6.63 | 6.63 | 6.63 | 6.63 | 6.63 |
| O2/CH4 mole ratio | .0784 | .0784 | .0784 | .1510 | .1510 | .1510 | .1510 | .1510 | .1510 | .1510 |
| Conv. of Oxygen, mole % | 99.0 | 99.5 | 99.5 | 1.7 | 9.4 | 28.3 | 75.0 | 96.5 | 99.5 | 99.5 |
| Conv. of CH4, mole % (1) | 12.5 | 12.8 | 13.4 | 0.1 | 0.9 | 3.6 | 11.3 | 15.9 | 17.2 | 18.9 |
| Residence Time, sec. | .090 | .086 | .082 | .386 | .358 | .338 | .318 | .303 | .289 | .276 |
| Selectivity, mole % | | | | | | | | | | |
| H2 | — | 8.1 | 13.1 | — | — | 51.9 | 35.8 | — | 11.6 | 15.4 |
| CO | 1.5 | — | 3.8 | 18.0 | 33.9 | 29.0 | 12.1 | 2.5 | 3.1 | 6.3 |
| CO2 | 19.3 | 18.5 | 17.6 | 82.0 | 66.1 | 55.5 | 46.5 | 35.5 | 32.8 | 29.8 |
| C2H4 | 28.1 | 32.5 | 35.4 | — | — | 1.5 | 10.5 | 22.7 | 28.7 | 32.8 |
| C2H6 | 45.9 | 44.0 | 37.5 | — | — | 14.0 | 28.2 | 34.4 | 30.7 | 26.4 |
| C2H2 | — | — | — | — | — | — | — | — | — | — |

TABLE VIII-continued

Li/Mg/Al(sol) (30% alumina)

| | Run | | | | | | | | | |
|---|---|---|---|---|---|---|---|---|---|---|
| | 77 | 78 | 79 | 81 | 82 | 83 | 84 | 85 | 86 | 87 |
| C3H8 & C3H6 | 4.3 | 3.9 | 3.6 | — | — | — | 2.0 | 4.0 | 3.1 | 3.0 |
| i-C4= | 0.5 | 0.8 | 1.6 | — | — | — | 0.7 | 0.6 | 1.3 | 1.2 |
| l-C4 | 0.3 | 0.1 | 0.1 | — | — | — | — | 0.4 | — | — |
| n-C4 | 0.2 | 0.3 | 0.4 | — | — | — | — | — | 0.3 | 0.5 |
| Unk (C4) | — | — | — | — | — | — | — | — | — | — |
| Unk (C5) | — | — | — | — | — | — | — | — | — | — |
| Unk (C6) | — | — | — | — | — | — | — | — | — | — |
| Sel. to C2+, mole % | 79.3 | 81.6 | 78.6 | 0 | 0 | 15.5 | 41.4 | 62.1 | 64.1 | 63.9 |
| C2H4/C2H6 | .613 | .738 | .943 | — | — | .108 | .372 | .659 | .936 | 1.244 |
| H2/CO | 0 | 1/B2/ | 3.460 | 0 | 0 | 1.788 | 2.952 | 0 | 3.758 | 2.438 |
| CO/CO2 | .078 | 0 | .216 | .214 | .512 | .524 | .261 | .071 | .094 | .211 |

TABLE IX

Li/Mg/Al(sol) (70% alumina)

| | Run | | | | | | | |
|---|---|---|---|---|---|---|---|---|
| | 2 | 3 | 4 | 5 | 6 | 7 | 8 | 9 |
| Temp. °C. (avg.) | 510 | 554 | 611 | 657 | 707 | 748 | 796 | 845 |
| SV (hr−1) | 1230 | 1230 | 1230 | 1230 | 1230 | 1230 | 1230 | 1230 |
| CH4/O2 mole ratio | 20.2 | 20.2 | 20.2 | 20.2 | 20.2 | 20.2 | 20.2 | 20.2 |
| O2/CH4 mole ratio | .0496 | .0496 | .0496 | .0496 | .0496 | .0496 | .0496 | .0496 |
| Conv. of Oxygen, mole % | 11.7 | 38.4 | 95.0 | 99.5 | 99.4 | 99.1 | 99.5 | 99.5 |
| Conv. of CH4, mole % (1) | 0.5 | 1.6 | 4.0 | 4.5 | 5.1 | 5.9 | 6.5 | 7.0 |
| Residence Time, sec. | .408 | .386 | .362 | .344 | .326 | .313 | .299 | .286 |
| Selectivity, mole % | | | | | | | | |
| H2 | — | 48.4 | 98.5 | 81.0 | 36.6 | 34.6 | 31.6 | 46.9 |
| CO | 49.8 | 41.2 | 34.3 | 27.0 | 18.5 | 12.6 | 10.8 | 17.3 |
| CO2 | 50.2 | 58.8 | 62.0 | 57.9 | 48.2 | 38.4 | 31.7 | 29.2 |
| C2H4 | — | — | — | 1.2 | 8.7 | 16.6 | 24.7 | 29.7 |
| C2H6 | — | — | 3.8 | 12.3 | 24.0 | 30.5 | 30.2 | 19.7 |
| C2H2 | — | — | — | — | — | — | — | — |
| C3H8 & C3H6 | — | — | — | 0.2 | 0.6 | 1.1 | 1.6 | 2.1 |
| i-C4= | — | — | — | — | — | 0.8 | 1.0 | 2.0 |
| l-C4 | — | — | — | — | — | — | — | — |
| n-C4 | — | — | — | — | — | — | — | — |
| Unk (C4) | — | — | — | 1.4 | — | — | — | — |
| Unk (C5) | — | — | — | — | — | — | — | — |
| Unk (C6) | — | — | — | — | — | — | — | — |
| Sel. to C2+, mole % | 0 | 0 | 3.8 | 15.1 | 33.3 | 49.0 | 57.5 | 53.5 |
| C2H4/C2H6 | — | — | 0 | .102 | .361 | .545 | .817 | 1.509 |

TABLE X

Li/Mg/Al(sol) (15% alumina)

| | 2 | 3 | 4 | 5 | 8 | 9 | 10 |
|---|---|---|---|---|---|---|---|
| Temp. °C. (avg.) | 493 | 599 | 645 | 684 | 693 | 741 | 788 |
| SV (hr−1) | 1230 | 1230 | 1230 | 1230 | 1230 | 1230 | 1230 |
| CH4/O2 mole ratio | 20.6 | 20.6 | 20.6 | 20.6 | 20.5 | 20.5 | 20.5 |
| O2/CH4 mole ratio | .0486 | .0486 | .0486 | .0486 | .0489 | .0489 | .0489 |
| Conv. of Oxygen, mole % | 43.8 | 98.4 | 99.1 | 99.0 | 99.1 | 99.0 | 99.2 |
| Conv. of CH4, mole % (1) | .01 | 4.4 | 6.9 | 8.2 | 8.8 | 9.0 | 8.7 |
| Residence Time, sec. | .418 | .367 | .348 | .334 | .331 | .315 | .301 |
| Selectivity, mole % | | | | | | | |
| H2 | — | 62.2 | — | — | — | — | — |
| CO | — | 17.9 | 2.6 | .006 | .05 | 0.5 | 0.6 |
| CO2 | — | 36.5 | 24.3 | 17.2 | 14.4 | 13.5 | 16.5 |
| C2H4 | — | 5.3 | 16.4 | 23.5 | 26.0 | 29.9 | 34.2 |
| C2H6 | 100 | 36.2 | 50.4 | 53.2 | 52.9 | 49.3 | 41.8 |
| C2H2 | — | — | — | — | — | — | — |
| C3H8 & C3H6 | — | 1.8 | 4.3 | 5.3 | 5.6 | 4.9 | 4.5 |
| i-C4= | — | 2.3 | 2.0 | 0.8 | 1.1 | 1.5 | 1.8 |
| l-C4 | — | — | — | — | — | 0.2 | 0.2 |
| n-C4 | — | — | — | — | — | 0.5 | 0.4 |
| Unk (C4) | — | — | — | — | — | — | — |
| Unk (C5) | — | — | — | — | — | — | — |
| Unk (C6) | — | — | — | — | — | — | — |
| Sel. to C2+, mole % | 100 | 45.6 | 73.1 | 82.8 | 85.6 | 86.1 | 82.9 |
| C2H4/C2H6 | 0 | .147 | .326 | .441 | .492 | .606 | .820 |

TABLE XI

Li/Mg/Al/(sol) (15% alumina) (Li/Mg = 1.2)

| | Run | | | | | | | | | |
|---|---|---|---|---|---|---|---|---|---|---|
| | 3 | 4 | 5 | 6 | 7 | 8 | 10 | 11 | 12 | 13 |
| Temp. °C. (avg.) | 505 | 610 | 609 | 609 | 669 | 708 | 722 | 710 | 759 | 810 |
| SV (hr−1) | 1230 | 1230 | 1230 | 1230 | 1230 | 1230 | 1230 | 1230 | 1230 | 1230 |
| CH4/O2 mole ratio | 20.4 | 20.4 | 20.4 | 20.4 | 20.4 | 20.4 | 19.6 | 19.6 | 19.6 | 19.6 |
| O2/CH4 mole ratio | .0490 | .0490 | .0490 | .0490 | .0490 | .0490 | .0511 | .0511 | .0511 | .0511 |
| Conv. of Oxygen, mole % | 22.7 | 94.8 | 92.9 | 92.1 | 99.2 | 99.4 | 99.3 | 98.8 | 99.3 | 99.4 |
| Conv. of CH4, mole % (1) | 0.1 | 3.1 | 5.1 | 5.3 | 7.6 | 8.9 | 9.2 | 8.9 | 9.3 | 9.8 |
| Residence Time, sec. | .411 | .362 | .362 | .362 | .339 | .326 | .321 | .325 | .310 | .295 |
| Selectivity, mole % | | | | | | | | | | |
| H2 | 446 | 90.5 | 48.2 | 46.0 | — | — | — | — | — | — |
| CO | 100 | 13.3 | 14.1 | 13.8 | 0.25 | — | — | 0.5 | 0.25 | 0.9 |
| CO2 | — | 1.4 | 35.1 | 36.8 | 16.3 | 14.8 | 14.5 | 14.3 | 17.0 | 27.6 |
| C2H4 | — | 11.6 | 6.7 | 6.7 | 21.7 | 26.3 | 28.3 | 26.2 | 32.8 | 34.2 |
| C2H6 | — | 69.4 | 41.6 | 40.3 | 54.9 | 51.8 | 50.8 | 52.3 | 44.4 | 31.1 |
| C2H2 | — | — | — | — | — | — | — | — | — | — |
| C3H8 & C3H6 | — | 4.3 | 2.4 | 2.5 | 5.9 | 5.5 | 5.4 | 5.8 | 4.6 | 4.3 |
| i-C4= | — | — | — | — | 0.7 | 0.9 | 0.7 | 0.5 | .4 | 1.1 |
| l-C4 | — | — | — | — | 0.2 | 0.6 | 0.3 | 0.5 | .4 | 0.3 |
| n-C4 | — | — | — | — | — | — | — | — | .3 | 0.5 |
| Unk (C4) | — | — | — | — | — | — | — | — | — | — |
| Unk (C5) | — | — | — | — | — | — | — | — | — | — |
| Unk (C6) | — | — | — | — | — | — | — | — | — | — |
| Sel. to C2+, mole % | — | 85.3 | 50.7 | 49.5 | 83.4 | 85.2 | 85.5 | 85.2 | 82.8 | 71.5 |
| C2H4/C2H6 | — | .166 | .161 | .166 | .395 | .508 | .558 | .500 | .738 | 1.097 |
| H2/CO | 8.559 | 6.824 | 3.411 | 3.327 | 0 | 0 | 0 | 0 | 0 | 0 |
| CO/CO2 | 1/B2/ | 9.229 | 0.402 | .375 | .015 | 0 | 0 | .037 | .015 | .033 |

TABLE XII

Li/Mg/Al (sol) (15% alumina) (Li/Mg = 1.2)

| Run | 24 | 25 | 26 | 27 | 28 | 29 | 30 |
|---|---|---|---|---|---|---|---|
| Temp. ~C. (avg.) | 505 | 591 | 658 | 698 | 756 | 811 | 857 |
| SV (hr-1) | 1230 | 1230 | 1230 | 1230 | 1230 | 1230 | 1230 |
| CH4/O2 mole ratio | 10.6 | 10.6 | 10.6 | 10.6 | 10.6 | 10.6 | 10.6 |
| O2/CH4 mole ratio | .0946 | .0946 | .0946 | .0946 | .0946 | .0946 | .0946 |
| Conv. of Oxygen, mole % | 6.2 | 9.7 | 22.6 | 32.8 | 69.3 | 96.6 | 99.5 |
| Conv. of CH4, mole % (1) | 0 | 0.3 | 2.4 | 4.5 | 10.7 | 13.1 | 13.6 |
| Residence Time, sec. | .411 | .370 | .343 | .329 | .311 | .295 | .283 |
| Selectivity, mole % | | | | | | | |
| H2 | (4) | — | — | — | — | 5.8 | 17.4 |
| CO | (4) | — | 5.2 | 4.0 | 2.5 | 1.7 | 5.2 |
| CO2 | (4) | — | 15.5 | 22.3 | 26.2 | 20.7 | 29.6 |
| C2H4 | (4) | — | 11.1 | 16.7 | 28.6 | 43.6 | 41.4 |
| C2H6 | (4) | 100 | 66.6 | 55.0 | 37.2 | 26.6 | 17.3 |
| C2H2 | (4) | — | — | — | — | — | — |
| C3H8 & C3H6 | (4) | — | 1.8 | 2.1 | 3.9 | 5.3 | 5.2 |
| i-C4= | (4) | — | — | — | 1.0 | 0.6 | 0.4 |
| i-C4 | (4) | — | — | — | 0.7 | 0.9 | 0.2 |
| n-C4 | (4) | — | — | — | — | 0.6 | 0.7 |
| Unk (C4) | (4) | — | — | — | — | — | — |
| Unk (C5) | (4) | — | — | — | — | — | — |
| Unk (C6) | (4) | — | — | — | — | — | — |
| Sel. to C2+, mole % | (4) | 100.0 | 79.5 | 73.8 | 71.3 | 77.6 | 65.2 |
| C2H4/C2H6 | (4) | 0 | .166 | .305 | .769 | 1.640 | 2.394 |
| H2/CO | (4) | — | 0 | 0 | 0 | 3.342 | 3.313 |
| CO/CO2 | (4) | — | .333 | .178 | .097 | .178 | — |

TABLE XIII

K/Ba/Al (sol)

| Run | 2 | 3 | 4 | 5 | 6 | 7 | 8 | 9 |
|---|---|---|---|---|---|---|---|---|
| Temp. ~C. (avg.) | 504.0 | 586.5 | 625.5 | 684.0 | 736.0 | 791.0 | 834.0 | 877.0 |
| SV (hr-1) | 1624 | 1624 | 1624 | 1624 | 1624 | 1624 | 1624 | 1624 |
| CH4/O2 mole ratio | 10.062 | 10.062 | 10.062 | 10.062 | 10.062 | 10.062 | 10.062 | 10.062 |
| O2/CH4 mole ratio | .099 | .099 | .099 | .099 | .099 | .099 | .099 | .099 |
| O2 Conv., mole % | 1.48 | 2.53 | 5.78 | 14.90 | 36.19 | 99.13 | 99.42 | 99.37 |
| Conv. of CH4, mole % (2) | .41 | .03 | .20 | 1.35 | 4.53 | 10.30 | 9.83 | 9.45 |
| Conv. of CH4, mole % (1) | .01 | .33 | .36 | 1.65 | 4.93 | 11.31 | 10.87 | 11.40 |
| Residence Time, sec. | .306 | .277 | .265 | .249 | .236 | .224 | .215 | .207 |
| Selectivity, mole % | | | | | | | | |
| H2 | 4125.0 | 78.08 | 105.87 | 41.73 | 20.16 | 5.98 | 13.52 | 61.87 |
| CO | 0 | 21.78 | 15.70 | 14.29 | 4.93 | .64 | 3.23 | 29.43 |
| CO2 | 100.00 | 23.76 | 49.33 | 35.22 | 25.56 | 34.62 | 38.11 | 39.21 |
| C2H4 | 0 | 0 | 0 | 7.14 | 21.18 | 30.13 | 33.02 | 23.89 |
| C2H6 | 0 | 54.46 | 26.91 | 43.06 | 44.30 | 29.09 | 19.90 | 4.50 |

TABLE XIII-continued

K/Ba/Al (sol)

| Run | 2 | 3 | 4 | 5 | 6 | 7 | 8 | 9 |
|---|---|---|---|---|---|---|---|---|
| C2H2 | 0 | 0 | 0 | 0 | 0 | .05 | .19 | .28 |
| C3's | 0 | 0 | 8.07 | .30 | 3.77 | 3.82 | 3.80 | 2.41 |
| i-C4= | 0 | 0 | 0 | 0 | 0 | .37 | .44 | 0 |
| i-C4 | 0 | 0 | 0 | 0 | .26 | .27 | .11 | 0 |
| n-C4 | 0 | 0 | 0 | 0 | 0 | 0 | 0 | .28 |
| Unk 1 | 0 | 0 | 0 | 0 | 0 | 1.00 | 1.22 | 0 |
| Unk 2 | 0 | 0 | 0 | 0 | 0 | 0 | 0 | 0 |
| Sel. to C2 | 0 | 54.45 | 34.98 | 50.50 | 69.51 | 64.74 | 58.67 | 31.36 |
| C2H4/C2H6 | 0 | 0 | 0 | .17 | .48 | 1.04 | 1.66 | 5.31 |
| H2/CO | 0 | 3.58 | 6.74 | 2.92 | 4.09 | 9.30 | 4.19 | 2.10 |
| CO/CO2 | 0 | .92 | .32 | .41 | .19 | .02 | .08 | .75 |

TABLE XIV

Li/Ca/Al (sol) (1//2/12.4% alumina)

| Run | 2 | 3 | 4 | 5 | 6 | 7 | 8 | 9 | 10 |
|---|---|---|---|---|---|---|---|---|---|
| Temp. ~C. (avg.) | 514 | 559 | 598 | 643 | 689 | 724 | 772 | 831 | 680 |
| SV (hr-1) | 1215 | 1215 | 1215 | 1215 | 1215 | 1215 | 1215 | 1215 | 1215 |
| CH4/O2 mole ratio | 10.88 | 10.88 | 10.88 | 10.88 | 10.88 | 10.88 | 10.88 | 10.88 | 10.88 |
| O2/CH4 mole ratio | .0919 | .0919 | .0919 | .0919 | .0919 | .0919 | .0919 | .0919 | .0919 |
| Conv. of Oxygen, mole % | 41.8 | 36.5 | 56.8 | 46.2 | 62.1 | 81.4 | 96.8 | 98.8 | 41.6 |
| Conv. of CH4, mole % (1) | 0.3 | 0.6 | 1.5 | 2.3 | 6.2 | 13.5 | 16.4 | 17.5 | 5.6 |
| Conv. of CH4, mole % (2) | 13.0 | 4.2 | 6.4 | 5.8 | 9.5 | 13.0 | 14.3 | 14.2 | 7.8 |
| Residence Time, sec. | .411 | .389 | .371 | .353 | .337 | .325 | .310 | .293 | .340 |
| Selectivity, mole % | | | | | | | | | |
| H2 | 1542 | 572 | 317 | 109.3 | 39.7 | 23.9 | 6.2 | 5.1 | 13.1 |
| CO | 59.0 | 76.2 | 28.9 | 12.4 | 2.5 | 1.3 | 1.0 | 1.3 | 1.9 |
| CO2 | — | 3.2 | 4.0 | 2.3 | 2.8 | 28.6 | 35.8 | 46.9 | 7.1 |
| C2H4 | — | — | 7.3 | 12.6 | 27.7 | 27.6 | 30.9 | 28.6 | 24.6 |
| C2H6 | 41.0 | 20.6 | 55.3 | 70.3 | 61.7 | 36.2 | 26.7 | 18.7 | 62.0 |
| C2H2 | — | — | — | — | — | — | — | — | — |
| C3H8 & C3H6 | — | — | 0.8 | 1.5 | 4.7 | 4.7 | 4.3 | 3.8 | 3.9 |
| i-C4= | — | — | 3.6 | 1.0 | 0.2 | 0.6 | 0.3 | 0.2 | — |
| i-C4 | — | — | — | — | 0.4 | 0.9 | 0.7 | 0.2 | 0.5 |
| n-C4 | — | — | — | — | — | — | 0.4 | 0.4 | — |
| Unk (C4) | — | — | — | — | — | — | — | — | — |
| Unk (C5) | — | — | — | — | — | — | — | — | — |
| Unk (C6) | — | — | — | — | — | — | — | — | — |
| Sel. to C2+, mole % | 41.0 | 20.6 | 67.0 | 85.4 | 94.7 | 70.0 | 63.3 | 51.9 | 91.0 |
| C2H4/C2H6 | 0 | 0 | .132 | .179 | .450 | .764 | 1.448 | 1.531 | 0.397 |
| H2/CO | 26.71 | 7.490 | 10.97 | 8.829 | 15.67 | 18.18 | 6.453 | 4.018 | 7.013 |
| CO/CO2 | 1/B2/ | 23.93 | 7.182 | 5.378 | .920 | .046 | .027 | .027 | .261 |

TABLE XV

Li/Mg/Si (sol)

| Run | 3 | 4 | 5 | 7 | 8 | 9 | 10 | 12 | 13 | 14 |
|---|---|---|---|---|---|---|---|---|---|---|
| Temp. ~C. (avg.) | 500.0 | 612.0 | 649.0 | 748.0 | 749.0 | 700.0 | 824.0 | 794.0 | 793.0 | 795.0 |
| SV (hr-1) | 1687 | 1687 | 1687 | 1687 | 1687 | 1687 | 1687 | 1687 | 1687 | 1687 |
| CH4/O2 mole ratio | 10.960 | 10.960 | 10.960 | 10.960 | 10.960 | 10.960 | 10.960 | 10.856 | 10.856 | 10.856 |
| O2/CH4 mole ratio | .091 | .091 | .091 | .091 | .091 | .091 | .091 | .092 | .092 | .092 |
| Conv. of Oxygen, mole % | −.01 | 14.44 | 26.50 | 94.46 | 95.65 | 61.03 | 99.00 | 99.62 | 99.11 | 99.13 |
| Conv. of CH4, mole % (2) | .32 | 1.59 | 3.44 | 14.29 | 14.02 | 8.86 | 15.21 | 14.98 | 14.96 | 14.92 |
| Conv. of CH4, mole % (1) | .03 | 1.75 | 3.54 | 13.82 | 13.90 | 9.29 | 15.04 | 15.42 | 15.08 | 14.90 |
| Residence Time, sec. | .300 | .262 | .251 | .227 | .227 | .238 | .211 | .217 | .217 | .217 |
| Selectivity, mole % | | | | | | | | | | |
| H2 | 458.89 | 79.93 | 57.89 | 20.86 | 20.68 | 29.56 | 18.29 | 16.58 | 18.27 | 18.49 |
| CO | 0 | 28.27 | 18.40 | 4.05 | 4.00 | 7.49 | 2.86 | 2.47 | 2.75 | 2.75 |
| CO2 | 100.0 | 38.22 | 28.40 | 19.48 | 19.43 | 20.60 | 17.18 | 16.72 | 17.63 | 17.75 |
| C2H4 | 0 | 1.83 | 7.69 | 35.38 | 35.45 | 22.86 | 41.90 | 37.87 | 39.74 | 40.58 |
| C2H6 | 0 | 31.68 | 44.36 | 34.96 | 34.90 | 43.32 | 30.36 | 32.54 | 31.54 | 31.96 |
| C2H2 | 0 | 0 | 0 | .12 | .09 | 0 | .25 | .11 | .24 | .23 |
| C3's | 0 | 0 | 1.15 | 4.59 | 4.76 | 3.26 | 4.98 | 4.59 | 4.71 | 4.85 |
| i-C4= | 0 | 0 | 0 | 0 | 0 | 0 | .28 | 2.39 | .50 | .20 |
| i-C4 | 0 | 0 | 0 | .60 | .61 | 1.42 | .51 | 1.02 | .89 | .18 |
| n-C4 | 0 | 0 | 0 | 0 | 0 | 0 | 0 | 0 | 0 | 0 |
| Unk 1 | 0 | 0 | 0 | .82 | .76 | 1.06 | 1.69 | 2.29 | 2.00 | 1.50 |
| Unk 2 | 0 | 0 | 0 | 0 | 0 | 0 | 0 | 0 | 0 | 0 |
| Sel. to C2, mole % | 0 | 33.51 | 53.20 | 76.48 | 76.57 | 71.92 | 79.97 | 80.81 | 79.62 | 79.49 |
| C2H4/C2H6 | 0 | .06 | .17 | 1.01 | 1.02 | .53 | 1.38 | 1.16 | 1.26 | 1.27 |
| H2/CO | 0 | 2.83 | 3.15 | 5.15 | 5.17 | 3.95 | 6.41 | 6.72 | 6.64 | 6.73 |
| CO/CO2 | 0 | .74 | .65 | .21 | .21 | .36 | .17 | .15 | .16 | .16 |

| Run | 15 | 16 | 19 | 20 | 21 | 22 | 23 | 24 |
|---|---|---|---|---|---|---|---|---|
| Temp. ~C. (avg.) | 796.0 | 801.0 | 800.0 | 800.0 | 800.0 | 801.0 | 801.0 | 801.0 |

TABLE XV-continued

| | Li/Mg/Si (sol) | | | | | | | |
|---|---|---|---|---|---|---|---|---|
| SV (hr-1) | 1687 | 1687 | 1690 | 1690 | 1690 | 1690 | 1690 | 1690 |
| CH4/O2 mole ratio | 10.856 | 10.856 | 10.799 | 10.799 | 10.798 | 10.798 | 10.798 | 10.798 |
| O2/CH4 mole ratio | .092 | .092 | .093 | .093 | .093 | .093 | .093 | .093 |
| Conv. of Oxygen, mole % | 99.45 | 99.26 | 99.05 | 99.31 | 98.06 | 99.16 | −264.3 | 99.70 |
| Conv. of CH4, mole % (2) | 14.89 | 14.92 | 15.07 | 14.99 | 14.85 | 14.59 | 13.85 | 14.29 |
| Conv. of CH4, mole % (1) | 15.46 | 14.90 | 14.96 | 15.04 | 15.11 | 14.97 | 15.38 | 15.28 |
| Residence Time, sec. | .217 | .216 | .215 | .215 | .215 | .215 | .215 | .215 |
| Selectivity, mole % | | | | | | | | |
| H2 | 17.85 | 18.50 | 18.47 | 18.45 | 18.37 | 18.79 | 18.21 | 18.40 |
| CO | 2.67 | 2.72 | 2.82 | 2.77 | 2.81 | 2.86 | 2.87 | 2.79 |
| CO2 | 17.09 | 17.62 | 17.59 | 17.54 | 17.48 | 17.65 | 17.35 | 17.37 |
| C2H4 | 38.97 | 40.75 | 40.46 | 40.39 | 40.14 | 40.53 | 39.87 | 39.95 |
| C2H6 | 30.96 | 32.02 | 31.57 | 31.46 | 31.47 | 32.04 | 31.49 | 31.62 |
| C2H2 | .23 | .24 | 0 | .23 | .20 | .19 | .25 | .21 |
| C3's | 4.55 | 4.78 | 4.74 | 4.67 | 4.53 | 4.74 | 4.65 | 4.75 |
| i-C4= | 1.15 | 0 | .57 | 0 | .52 | .30 | .16 | .88 |
| i-C4 | 1.41 | .39 | .86 | .59 | .72 | .22 | 1.23 | .65 |
| n-C4 | 0 | 0 | 1.39 | 0 | 0 | 0 | 0 | 0 |
| Unk 1 | 2.97 | 1.47 | 0 | 2.08 | 2.14 | 1.47 | 2.12 | 1.77 |
| Unk 2 | 0 | 0 | 0 | 0 | 0 | 0 | 0 | 0 |
| Sel. to C2, mole % | 80.24 | 79.66 | 79.59 | 79.69 | 79.71 | 79.49 | 79.78 | 79.83 |
| C2H4/C2H6 | 1.26 | 1.27 | 1.28 | 1.28 | 1.28 | 1.27 | 1.27 | 1.26 |
| H2/CO | 6.68 | 6.80 | 6.56 | 6.66 | 6.53 | 6.57 | 6.34 | 6.58 |
| CO/CO2 | .16 | .15 | .16 | .16 | .16 | .16 | .17 | .16 |

TABLE XVI

| | Li/Mg/Si (sol) (15% SiO2) | | | | | | | | | |
|---|---|---|---|---|---|---|---|---|---|---|
| Run | 13 | 14 | 16 | 17 | 18 | 20 | 21 | 22 | 23 | 24 |
| Temp. ~C. (avg.) | 886 | 933 | 530 | 633 | 695 | 707 | 750 | 798 | 849 | 890 |
| SV (hr-1) | 1249 | 1249 | 2471 | 2471 | 2471 | 2471 | 2471 | 2471 | 2471 | 2471 |
| CH4/O2 mole ratio | 19.7 | 19.7 | 20.5 | 20.5 | 20.5 | 19.9 | 19.9 | 19.9 | 19.9 | 19.9 |
| O2/CH4 mole ratio | .0507 | .0507 | .0488 | .0488 | .0488 | .0504 | .0504 | .0504 | .0504 | .0504 |
| Conv. of Oxygen, mole % | 99.5 | 99.5 | 3.8 | 30.0 | 75.3 | 84.3 | 98.9 | 99.5 | 99.5 | 99.5 |
| Conv. of CH4, mole % (1) | 8.8 | 8.0 | .06 | 1.4 | 5.6 | 6.6 | 8.6 | 9.4 | 9.6 | 9.4 |
| Residence Time, sec. | .272 | .261 | .198 | .176 | .164 | .162 | .156 | .149 | .142 | .137 |
| Selectivity, mole % | | | | | | | | | | |
| H2 | 30.7 | 86.1 | — | — | 18.3 | 12.5 | 10.2 | 9.1 | 12.2 | 22.6 |
| CO | 8.9 | 29.5 | 100 | 3.12 | 7.9 | 6.1 | 3.4 | 2.8 | 3.4 | 6.4 |
| CO2 | 17.1 | 18.6 | — | 14.3 | 23.5 | 22.0 | 18.3 | 14.5 | 13.1 | 14.0 |
| C2H4 | 49.6 | 39.5 | — | 3.8 | 16.5 | 18.9 | 29.1 | 33.6 | 41.0 | 47.2 |
| C2H6 | 17.1 | 65.0 | — | 50.7 | 49.2 | 48.4 | 44.5 | 44.0 | 37.5 | 26.2 |
| C2H2 | — | — | — | — | — | — | — | — | — | — |
| C3H8 & C3H6 | 5.8 | 4.5 | — | — | 2.9 | 3.3 | 3.8 | 3.8 | 4.2 | 4.9 |
| i-C4= | 1.1 | 1.2 | — | — | — | 1.1 | 0.2 | 0.8 | 0.4 | 0.9 |
| i-C4 | — | — | — | — | — | — | 0.4 | 0.2 | — | — |
| n-C4 | 0.5 | 0.2 | — | — | — | 0.2 | 0.2 | 0.4 | 0.4 | 0.5 |
| Unk (C4) | — | — | — | — | — | — | — | — | — | — |
| Unk (C5) | — | — | — | — | — | — | — | — | — | — |
| Unk (C6) | — | — | — | — | — | — | — | — | — | — |
| Sel. to C2+, mole % | 74.1 | 51.9 | 0 | 54.5 | 68.6 | 71.9 | 78.2 | 82.8 | 83.5 | 79.7 |
| C2H4/C2H6 | 2.890 | 6.042 | — | .076 | .335 | .391 | .653 | .763 | 1.095 | 1.803 |
| H2/CO | 3.451 | 2.915 | 0 | 0 | 2.324 | 2.038 | 2.961 | 3.264 | 3.639 | 3.531 |
| CO/CO2 | 0.521 | 1.588 | 1/B2/ | 2.189 | .335 | .278 | .187 | .193 | .256 | .456 |

TABLE XVII

| | Li/Mg/Si | | | | | | |
|---|---|---|---|---|---|---|---|
| Run | 4 | 5 | 6 | 7 | 8 | 9 | 11 |
| Temp. ~C. (avg.) | 405 | 476 | 524 | 565 | 613 | 658 | 726 |
| SV (hr-1) | 160 | 160 | 160 | 160 | 160 | 160 | 160 |
| CH4/O2 mole ratio | 1.530 | 1.53 | 1.53 | 1.53 | 1.53 | 1.53 | 1.56 |
| O2/CH4 mole ratio | .654 | .654 | .654 | .654 | .654 | .654 | .641 |
| Conv. of Oxygen, mole % | 4.5 | 8.2 | 22.8 | 11.0 | 10.3 | 24.9 | 71.8 |
| Conv. of CH4, mole % (1) | 2.6 | 3.9 | 11.3 | 5.5 | 5.7 | 13.8 | 33.7 |
| Conv. of CH4, mole % (2) | 2.2 | 4.7 | 12.1 | 6.3 | 6.8 | 14.4 | 32.8 |
| Residence Time, sec. | 3.93 | 3.56 | 3.35 | 3.18 | 3.01 | 2.87 | 2.67 |
| Selectivity, mole % | | | | | | | |
| H2 | 29.1 | 74.3 | 47.5 | 82.4 | 76.4 | 48.7 | 29.4 |
| CO | 35.8 | 48.5 | 48.6 | 60.4 | 64.6 | 64.2 | 66.5 |
| CO2 | 64.2 | 51.5 | 51.4 | 39.6 | 28.6 | 17.4 | 17.8 |
| C2H4 | — | — | — | — | — | 11.0 | 12.3 |
| C2H6 | — | — | — | — | 6.8 | 7.0 | 2.5 |
| C2H2 | — | — | — | — | — | — | — |
| C3H8 & C3H6 | — | — | — | — | — | 0.4 | 1.0 |
| i-C4= | — | — | — | — | — | — | — |

TABLE XVII-continued

| | Li/Mg/Si | | | | | | |
|---|---|---|---|---|---|---|---|
| i-C4 | — | — | — | — | — | — | — |
| n-C4 | — | — | — | — | — | — | — |
| Unk (C4) | — | — | — | — | — | — | — |
| Unk (C5) | — | — | — | — | — | — | — |
| Unk (C6) | — | — | — | — | — | — | — |
| Sel. to C2+, mole % | 0 | 0 | 0 | 0 | 6.8 | 18.4 | 15.8 |
| C2H4/C2H6 | — | — | — | — | 0 | 1.571 | 5.00 |
| H2/CO Ratio | 0.813 | 1.534 | .977 | 1.820 | 1.184 | .759 | .426 |

| Run | 12 | 13 | 14 | 15 | 16 | 17 | 28 |
|---|---|---|---|---|---|---|---|
| Temp. ~C. (avg.) | 767 | 822 | 873 | 921 | 969 | 1024 | 1064 |
| SV (hr-1) | 160 | 160 | 160 | 160 | 160 | 160 | 160 |
| CH4/O2 mole ratio | 1.56 | 1.56 | 1.56 | 1.56 | 1.56 | 1.56 | 1.56 |
| O2/CH4 mole ratio | .641 | .641 | .641 | .641 | .641 | .641 | .641 |
| Conv. of Oxygen, mole % | 98.6 | 99.3 | 99.0 | 98.8 | 99.2 | 99.2 | 99.2 |
| Conv. of CH4, mole % (1) | 42.9 | 46.9 | 49.7 | 51.3 | 53.5 | 58.4 | 64.9 |
| Conv. of CH4, mole % (2) | 43.1 | 46.5 | 50.1 | 53.4 | 56.6 | 63.9 | 72.8 |
| Residence Time, sec. | 2.57 | 2.44 | 2.33 | 2.23 | 2.15 | 2.06 | 2.00 |
| Selectivity, mole % | | | | | | | |
| H2 | 20.4 | 43.3 | 71.8 | 78.1 | 90.9 | 112.8 | 134.0 |
| CO | 63.0 | 66.1 | 68.7 | 73.9 | 75.4 | 77.2 | 80.6 |
| CO2 | 24.1 | 24.5 | 26.6 | 23.9 | 23.5 | 22.4 | 19.4 |
| C2H4 | 9.9 | 8.3 | 4.4 | 2.2 | 1.1 | 0.4 | — |
| C2H6 | 2.5 | 0.9 | 0.3 | — | — | — | — |
| C2H2 | — | — | — | — | — | — | — |
| C3H8 & C3H6 | 0.5 | 0.2 | — | — | — | — | — |
| i-C4= | — | — | — | — | — | — | — |
| i-C4 | — | — | — | — | — | — | — |
| n-C4 | — | — | — | — | — | — | — |
| Unk (C4) | — | — | — | — | — | — | — |
| Unk (C5) | — | — | — | — | — | — | — |
| Unk (C6) | — | — | — | — | — | — | — |
| Sel. to C2+, mole % | 12.9 | 9.4 | 4.7 | 2.2 | 1.1 | 0.4 | 0 |
| C2H4/C2H6 | 3.983 | 8.957 | 12.67 | 1/B2/ | 1/B2/ | 1/B2/ | 1/B2/ |
| H2/CO Ratio | .324 | .655 | .986 | 1.057 | 1.194 | 1.461 | 1.663 |

TABLE XVIII

| | Mg | | | | | | | | | | |
|---|---|---|---|---|---|---|---|---|---|---|---|
| Run | 5 | 6 | 7 | 8 | 9 | 10 | 12 | 13 | 14 | 15 | 16 |
| Temp. ~C. (avg.) | 458 | 543 | 611 | 664 | 718 | 755 | 759 | 803 | 845 | 868 | 645 |
| SV (hr-1) | 1733 | 1733 | 1733 | 1733 | 1733 | 1733 | 1733 | 1733 | 1733 | 1733 | 1733 |
| CH4/O2 mole ratio | 17.5 | 17.5 | 17.5 | 17.5 | 17.5 | 17.5 | 17.2 | 17.2 | 17.2 | 17.2 | 17.2 |
| Conv. of Oxygen, mole % | 4.2 | 32.7 | 69.7 | 99.1 | 99.3 | 99.3 | 99.3 | 99.3 | 99.3 | 99.3 | 60.0 |
| Conv. of CH4, mole % | 0.2 | 1.4 | 3.1 | 4.2 | 4.6 | 5.3 | 5.5 | 5.7 | 5.4 | 6.1 | 2.5 |
| Residence Time, sec. | 0.316 | .278 | .257 | .242 | .229 | .221 | .220 | .211 | .203 | .199 | — |
| Selectivity, mole % | | | | | | | | | | | |
| H2 | — | — | — | — | 38.8 | 33.6 | 35.2 | 40.5 | 74.1 | 114.2 | 95.4 |
| CO | 60 | 40 | 38.6 | 23.7 | 10.5 | 8.3 | 9.2 | 11.2 | 30.2 | 49.5 | 44.2 |
| CO2 | 40 | 60 | 59.9 | 61.4 | 53.0 | 43.4 | 42.6 | 40.0 | 39.1 | 30.5 | 49.7 |
| C2H4 | — | — | — | 1.7 | 6.8 | 12.0 | 12.6 | 15.6 | 13.1 | 9.5 | — |
| C2H6 | — | — | 1.6 | 13.2 | 29.2 | 35.6 | 34.9 | 32.4 | 17.2 | 10.1 | 6.1 |
| C2H2 | — | — | — | — | — | — | 0.1 | — | — | — | — |
| C3H8 & C3H6 | — | — | — | — | 0.5 | 0.8 | 0.5 | 0.8 | 0.4 | 0.4 | — |
| i-C4= | — | — | — | — | — | — | — | — | — | — | — |
| i-C4 | — | — | — | — | — | — | — | — | — | — | — |
| n-C4 | — | — | — | — | — | — | — | — | — | — | — |
| Unk (C4) | — | — | — | — | — | — | — | — | — | — | — |
| Unk (C5) | — | — | — | — | — | — | — | — | — | — | — |
| Unk (C6) | — | — | — | — | — | — | — | — | — | — | — |
| Sel. to C2+, mole % | 0 | 0 | 1.6 | 14.9 | 36.5 | 48.4 | 48.1 | 48.8 | 30.7 | 20.0 | 6.1 |
| C2H4/C2H6 | — | — | 0 | .126 | .217 | .336 | .361 | .482 | .762 | .901 | 0 |
| H2/CO | — | — | — | — | 3.68 | 4.03 | 3.81 | 3.61 | 2.45 | 2.31 | 2.159 |

TABLE XIX

| | Li/Mg | | | | | | | |
|---|---|---|---|---|---|---|---|---|
| Run | 3 | 4 | 5 | 6 | 7 | 8 | 9 | 10 |
| Temp. ~C. (avg.) | 532 | 574 | 627 | 676 | 723 | 778 | 821 | 849 |
| SV (hr-1) | 154 | 154 | 154 | 154 | 154 | 154 | 154 | 154 |

TABLE XIX-continued

| Run | Li/Mg | | | | | | | |
|---|---|---|---|---|---|---|---|---|
| | 3 | 4 | 5 | 6 | 7 | 8 | 9 | 10 |
| CH4/O2 mole ratio | 12.5 | 12.5 | 12.5 | 12.5 | 12.5 | 12.5 | 12.5 | 12.5 |
| Conv. of Oxygen, mole % | 1.6 | 3.8 | 13.7 | 33.2 | 71.0 | 97.0 | 98.8 | 99.1 |
| Conv. of CH4, mole % (1) | 0.1 | .3 | 1.6 | 3.8 | 7.3 | 9.6 | 9.5 | 11.3 |
| Conv. of CH4, mole % (2) | 0.3 | 0.6 | 1.7 | 3.5 | 7.7 | 8.3 | 8.3 | 9.1 |
| Residence Time, sec. | 3.46 | 3.28 | 3.09 | 2.93 | 2.80 | 2.65 | 2.53 | 2.48 |
| Selectivity, mole % | | | | | | | | |
| H2 | 292 | 128.9 | 52.3 | 32.0 | 24.0 | 47.9 | 73.8 | 74.9 |
| CO | 21.2 | 2.3 | 8.8 | 8.9 | 7.7 | 14.6 | 26.5 | 38.5 |
| CO2 | 9.4 | 28.2 | 20.9 | 20.2 | 32.1 | 37.0 | 35.5 | 36.4 |
| C2H4 | — | — | 14.5 | 25.3 | 30.2 | 31.3 | 28.6 | 20.3 |
| C2H6 | 69.4 | 69.5 | 54.1 | 41.8 | 24.4 | 12.0 | 5.4 | 2.3 |
| C3H8 & C3H6 | — | — | 1.6 | 3.2 | 4.3 | 3.8 | 3.4 | 2.2 |
| i-C4= | — | — | — | — | — | — | — | — |
| i-C4 | — | — | — | — | — | — | — | — |
| n-C4 | — | — | — | — | — | — | — | — |
| Unk (C4) | — | — | — | 0.6 | 1.4 | 1.3 | 0.7 | 0.4 |
| Unk (C5) | — | — | — | — | — | — | — | — |
| Unk (C6) | — | — | — | — | — | — | — | — |
| Sel. to C2+, mole % | 69.4 | 69.5 | 70.2 | 70.9 | 60.3 | 48.4 | 38.1 | 25.2 |
| C2H4/C2H6 | 0 | 0 | .269 | .604 | 1.234 | 1.602 | 5.306 | 8.978 |

(1) CH4 conversion calculated from carbon in products
(2) CH4 conversion calculated from CH4 in minus CH4 out
(4) Conversion too low for accurate measurement

What is claimed is:

1. A method of preparing a catalytic composition effective in the conversion of a feedstock alkane containing from 1 to 3 carbon atoms to a higher molecular weight hydrocarbon, said method comprising the steps of:
   thoroughly dispersing in an aqueous medium a mixture comprising a first material comprising a Group IA metal compound and a second material comprising a Group IIA metal compound, a sol comprising an aqueous suspension of a compound of a metal selected from the group consisting of aluminum, silicon, titanium, zinc, zirconium, cadmium and tin to form a slurry with the combination of said Group IA and said Group IIA metals being selected to be stable at oxidative coupling reaction conditions, and
   drying said slurry to evaporate substantially all of said aqueous medium and leaving behind a substantially dry solid material wherein said Group IA metal and said Group IIA metal are in an atomic ratio of about 0.5:1 to about 2:1 and said metal of said sol comprises about 1 wt. % to about 30 wt. % of said dry material.

2. The method of claim 1 wherein said sol comprises alumina.

3. The method of claim 2 wherein said catalytic composition comprises about 10 wt. % to about 20 wt. % alumina expressed as Al2O3.

4. The method of claim 1 wherein said catalytic composition comprises said Group IA metal and said Group IIA metal in an atomic ratio of about 0.8:1 to about 1.2:1.

5. The method of claim 1 wherein said catalytic composition is substantially free of a reducible metal oxide.

6. The method of claim 1 wherein said Group IA and Group IIA metals have similar ionic radii.

7. The method of claim 1 wherein said Group IA metal comprises lithium and said Group IIA metal is selected from the group consisting of magnesium and calcium.

8. The method of claim 1 wherein said Group IA metal comprises sodium and said Group IIA metal is selected from the group consisting of calcium and strontium.

9. The method of claim 1 wherein said Group IA metal comprises potassium and said Group IIA metal is selected from the group consisting of calcium, strontium and barium.

10. A method of preparing a catalytic composition effective in the conversion of a feedstock alkane containing from 1 to 3 carbon atoms to a higher molecular weight hydrocarbon, said method comprising the steps of:
    thoroughly dispersing in an aqueous medium a mixture comprising a first material comprising a Group IA metal compound and a second material comprising a Group IIA metal compound, a sol comprising an aqueous suspension of a compound of a metal selected from the group consisting of aluminum and silicon to form a slurry with the combination of said Group IA and said Group IIA metals being selected to be stable at oxidative coupling reaction conditions, and
    drying said slurry to evaporate substantially all of said aqueous medium and leaving behind a substantially dry solid material wherein said Group IA metal and said Group IIA metal are in an atomic ratio of about 0.5:1 to about 2:1 and said metal of said sol comprises about 1 wt. % to about 30 wt. % of said dry material.

11. The method of claim 10 wherein said catalytic composition comprises said Group IA metal and said Group IIA metal in an atomic ratio of about 0.8:1 to about 1.2:1.

12. The method of claim 10 wherein said catalytic composition is substantially free of a reducible metal oxide.

13. The method of claim 10 wherein said Group IA and Group IIA metal shave similar ionic radii.

14. The method of claim 10 wherein said Group IA metal comprises lithium and said Group IIA metal is selected from the group consisting of magnesium and calcium.

15. The method of claim 10 wherein said Group IA metal comprises sodium and said Group IIA metal is selected from the group consisting of calcium and strontium.

16. The method of claim 10 wherein said Group IA metal comprises potassium and said Group IIA metal is selected from the group consisting of calcium, strontium and barium.

17. A method of preparing a catalytic composition effective in the conversion of a feedstock alkane containing from 1 to 3 carbon atoms to a higher molecular weight hydrocarbon, said method comprising the steps of:
thoroughly dispersing in an aqueous medium a mixture comprising a first material comprising a Group IA metal compound and a second material comprising a Group IIA metal compound, a sol comprising alumina to form a slurry with the combination of said Group IA and said Group IIA metals being selected to be stable at oxidative coupling reaction conditions, and
drying said slurry to evaporate substantially all of said aqueous medium and leaving behind a substantially dry solid material wherein said Group IA metal and said Group IIA metal are in an atomic ratio of about 0.5:1 to about 2:1 and said metal of said sol comprises about 1 wt. % to about 30 wt. % of said dry material.

18. The method of claim 17 wherein said catalytic composition comprises about 10 wt. % to about 20 wt. % alumina expressed as $Al_2O_3$.

19. The method of claim 17 wherein said catalytic composition comprises said Group IA metal and said Group IIA metal in an atomic ratio of about 0.8:1 to about 1.2:1.

20. The method of claim 17 wherein said catalytic composition is substantially free of a reducible metal oxide.

21. The method of claim 17 wherein said Group IA and Group IIA metals have similar ionic radii.

22. The method of claim 17 wherein said Group IA metal comprises lithium and said Group IIA metal is selected from the group consisting of magnesium and calcium.

23. The method of claim 17 wherein said Group IA metal comprises sodium and said Group IIA metal is selected from the group consisting of calcium and strontium.

24. The method of claim 17 wherein said Group IA metal comprises potassium and said Group IIA metal is selected from the group consisting of calcium, strontium and barium.

25. A method of preparing a catalytic composition effective in the conversion of a feedstock alkane containing from 1 to 3 carbon atoms to a higher molecular weight hydrocarbon, said method comprising the steps of:
thoroughly dispersing in an aqueous medium a mixture comprising a first material comprising a Group IA metal compound and a second material comprising a Group IIA metal compound, a sol comprising alumina to form a slurry with the combination of said Group IA and said Group IIA metals being selected to be stable at oxidative coupling reaction conditions;
drying said slurry to evaporate substantially all of said aqueous medium and leaving behind a substantially dry solid material wherein said Group IA metal and said Group IIA metal are in an atomic ratio of about 0.5:1 to about 2:1 and said metal of said sol comprises about 1 wt. % to about 30 wt. % of said dry material, and
calcining said dry material.

* * * * *

UNITED STATES PATENT OFFICE
CERTIFICATE OF CORRECTION

Patent No. 4,992,409                          Dated February 12, 1991

Inventor(s) Glenn O. Michaels, Michael J. Spangler

It is certified that error appears in the above-identified patent and that said Letters Patent is hereby corrected as shown below:

Patent reads

| Col. | Line | |
|---|---|---|
| 6  | 48 | "from they" should be --from which they-- |
| 12 | 61 | "Table XVII" should be --Table XVIII-- |
| 13 | 10 | "Table XVIII" should be --Table XIX-- |
| 13 | 26 | "Table XIX" should be --Table XVII-- |
| 32 | 62 | "metal shave" should be --metals have-- |

Signed and Sealed this

Twenty-ninth Day of December, 1992

Attest:

DOUGLAS B. COMER

Attesting Officer        Acting Commissioner of Patents and Trademarks